(12) United States Patent
Campbell et al.

(10) Patent No.: US 6,245,026 B1
(45) Date of Patent: Jun. 12, 2001

(54) THERMOGRAPHY CATHETER

(75) Inventors: Thomas H. Campbell, Brentwood; William L. Sweet, Mountain View; David A. Rahdert, San Francisco, all of CA (US)

(73) Assignee: Farallon MedSystems, Inc., Brentwood, CA (US)

( * ) Notice: Subject to any disclaimer, the term of this patent is extended or adjusted under 35 U.S.C. 154(b) by 0 days.

(21) Appl. No.: 09/346,072

(22) Filed: Jul. 1, 1999

Related U.S. Application Data

(63) Continuation of application No. 08/895,757, filed on Jul. 17, 1997, now Pat. No. 5,924,997.
(60) Provisional application No. 60/107,693, filed on Nov. 9, 1998, and provisional application No. 60/023,289, filed on Jul. 29, 1996.

(51) Int. Cl.$^7$ .................................................. A61B 10/00
(52) U.S. Cl. ............................................................ 600/549
(58) Field of Search ................................... 600/585, 555, 600/549; 606/28

(56) References Cited

U.S. PATENT DOCUMENTS

| | | |
|---|---|---|
| 4,776,334 | 10/1988 | Priones . |
| 4,794,931 | 1/1989 | Yock . |
| 4,824,436 | 4/1989 | Wolinski . |
| 4,841,981 | 6/1989 | Tanabe et al. . |
| 4,883,459 | 11/1989 | Caldron . |
| 5,000,185 | 3/1991 | Yock . |
| 5,174,299 | 12/1992 | Nelson . |
| 5,279,565 | 1/1994 | Klein et al. . |
| 5,313,949 | 5/1994 | Yock . |
| 5,336,178 | 8/1994 | Kaplan et al. . |
| 5,373,849 | 12/1994 | Maroney et al. . |
| 5,496,311 | * 3/1996 | Abele et al. ............................. 606/28 |
| 5,542,915 | 8/1996 | Edwards et al. . |
| 5,542,928 | * 8/1996 | Evans et al. ............................. 604/113 |
| 5,547,472 | 8/1996 | Onishi et al. . |
| 5,558,093 | 9/1996 | Pomeranz . |
| 5,606,974 | 3/1997 | Castellanos et al. . |
| 5,682,899 | 11/1997 | Nashef et al. . |
| 5,849,028 | 12/1998 | Chen . |
| 5,865,788 | * 2/1999 | Edwards et al. ............................. 604/22 |

(List continued on next page.)

FOREIGN PATENT DOCUMENTS

97/10748   3/1997   (WO) .

OTHER PUBLICATIONS

W Casscells et al. "Thermal Detection of Cellular Infiltrates In Living Atherosclerotic Plaques: Possible Implications For Plaque Rupture And Thrombosis", May 25, 1996 *The Lancet*.

M J Davies "Detecting Vulnerable Coronary Plaques" May 25, 1996, *The Lancet*.

*Primary Examiner*—Eric F. Winakur
*Assistant Examiner*—Pamela L. Wingood
(74) *Attorney, Agent, or Firm*—Beyer Weaver & Thomas, LLP

(57) ABSTRACT

A variety of improved thermal mapping catheters are disclosed which are capable of sensing and mapping thermal variations within body vessels. In embodiments directed at vascular applications, the catheters are capable of detecting temperature variations in atherosclerotic plaque, on the atherosclerotic plaque surface, and on the arterial wall of aneurysms and other vascular lesions of the human vasculature. In one aspect of the invention, a combined thermal mapping and drug delivery catheter is provided. In this embodiment a plurality of thermal sensors are combined with at least one infusion port suitable for delivering therapeutic agents into a vessel. In some embodiments, at least some of the infusion ports are located between adjacent thermal sensors. The described catheters may be used in a variety of new applications and medical diagnostic and treatment techniques.

20 Claims, 11 Drawing Sheets

U.S. PATENT DOCUMENTS

| | | |
|---|---|---|
| 5,871,449 | 2/1999 | Brown . |
| 5,906,636 | 5/1999 | Casscells, III et al. . |
| 5,910,101 | 6/1999 | Andrews et al. . |
| 5,924,997 | 7/1999 | Campbell . |
| 5,925,016 | 7/1999 | Chornenky et al. . |
| 5,935,075 | 8/1999 | Casscells et al. . |

* cited by examiner

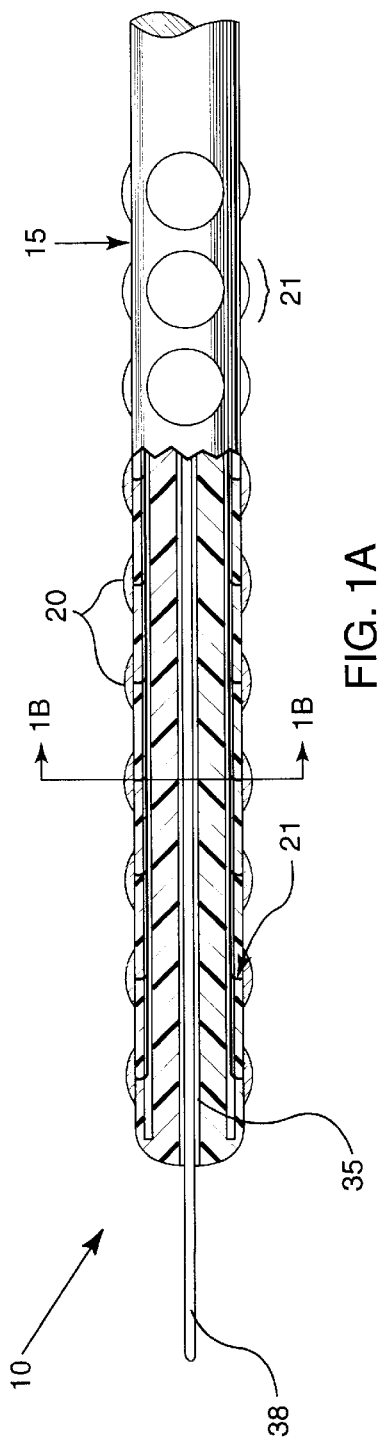
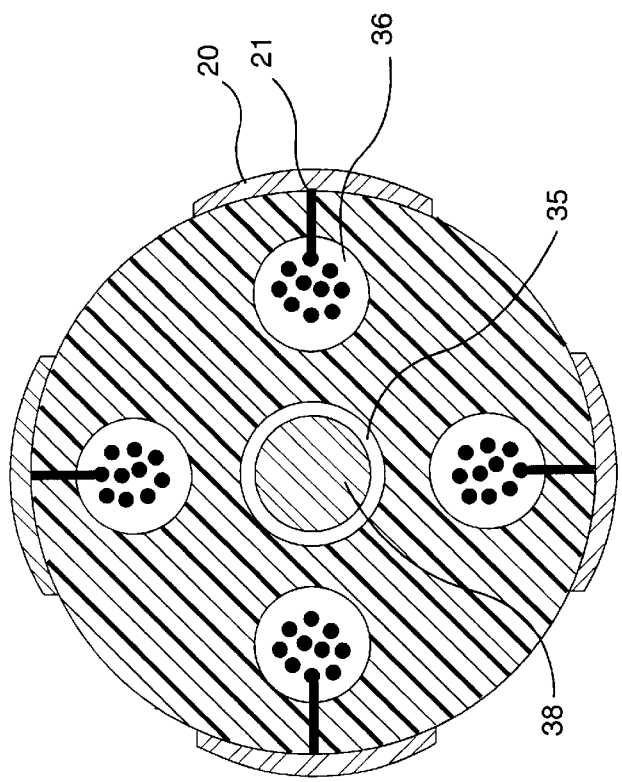
FIG. 1A
FIG. 1B

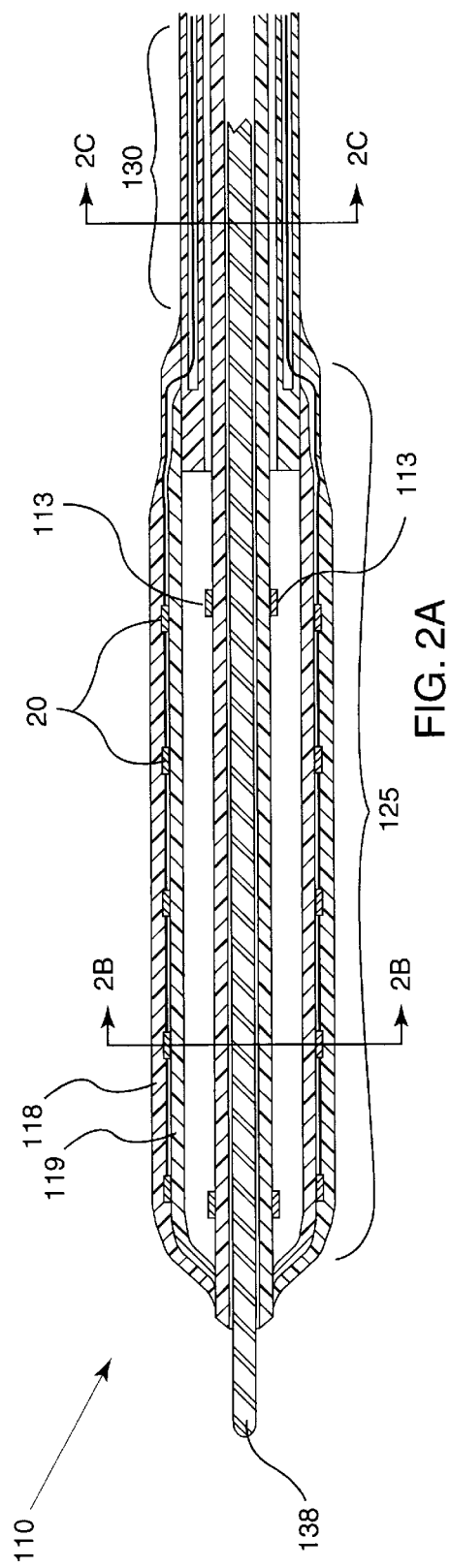
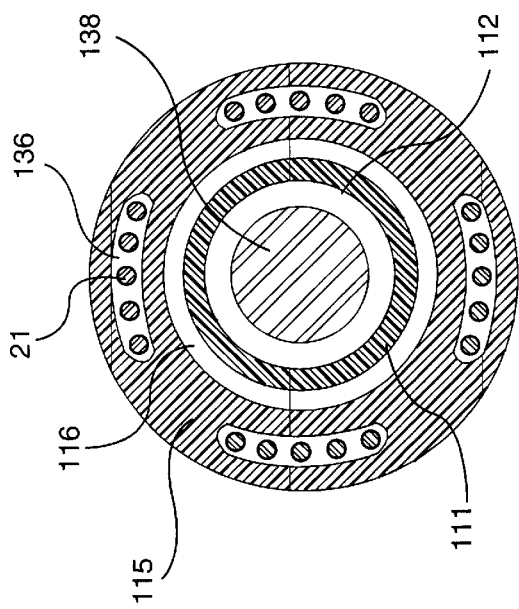
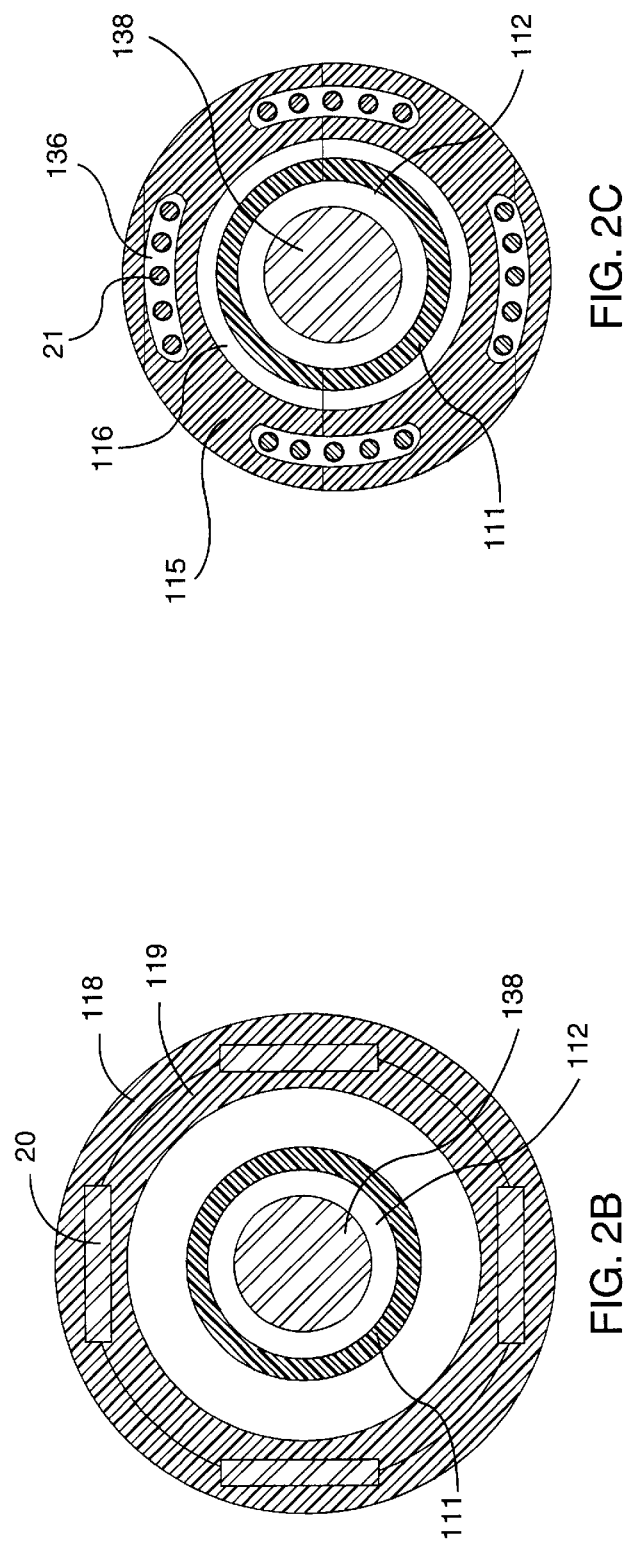

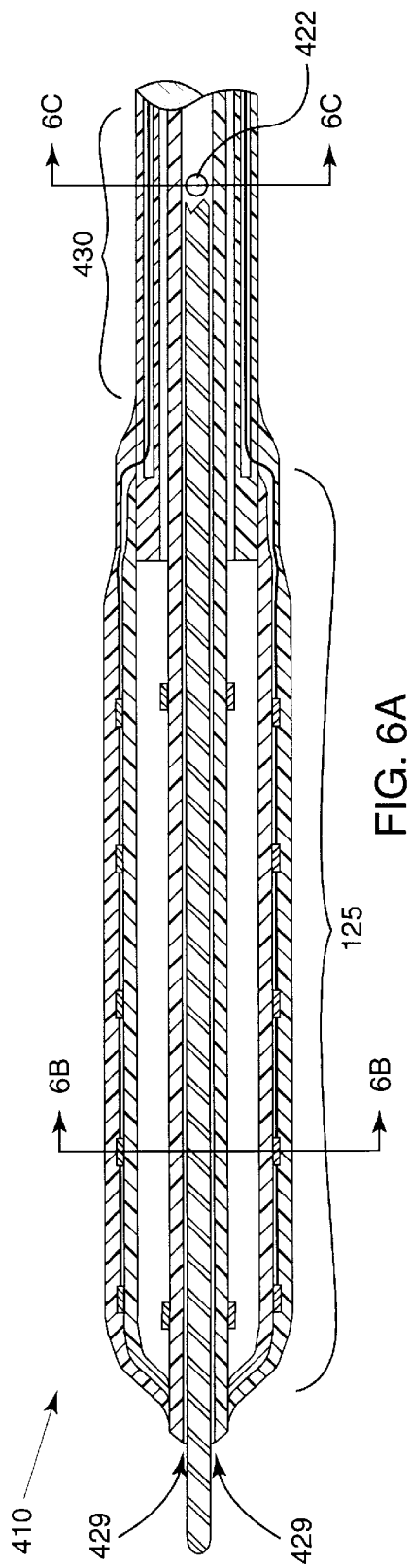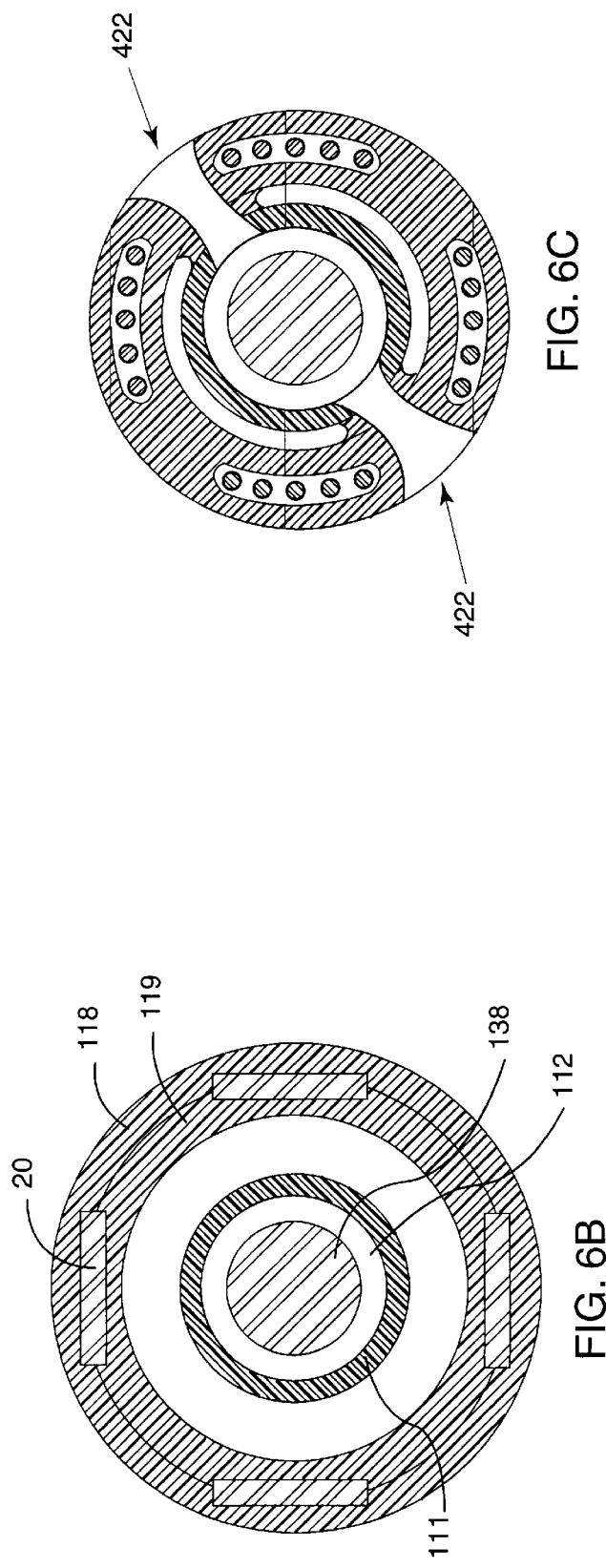

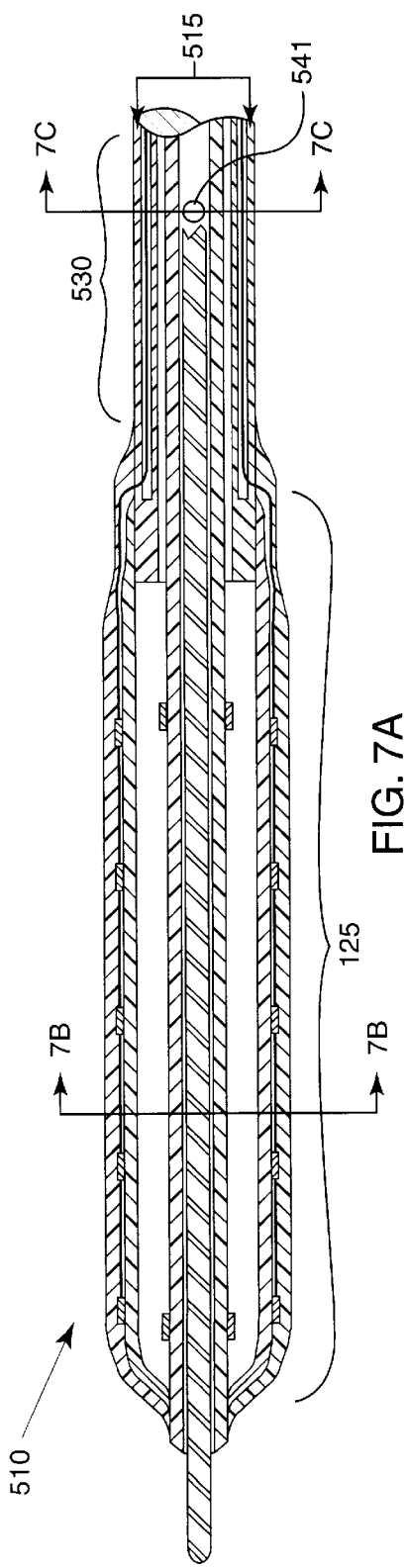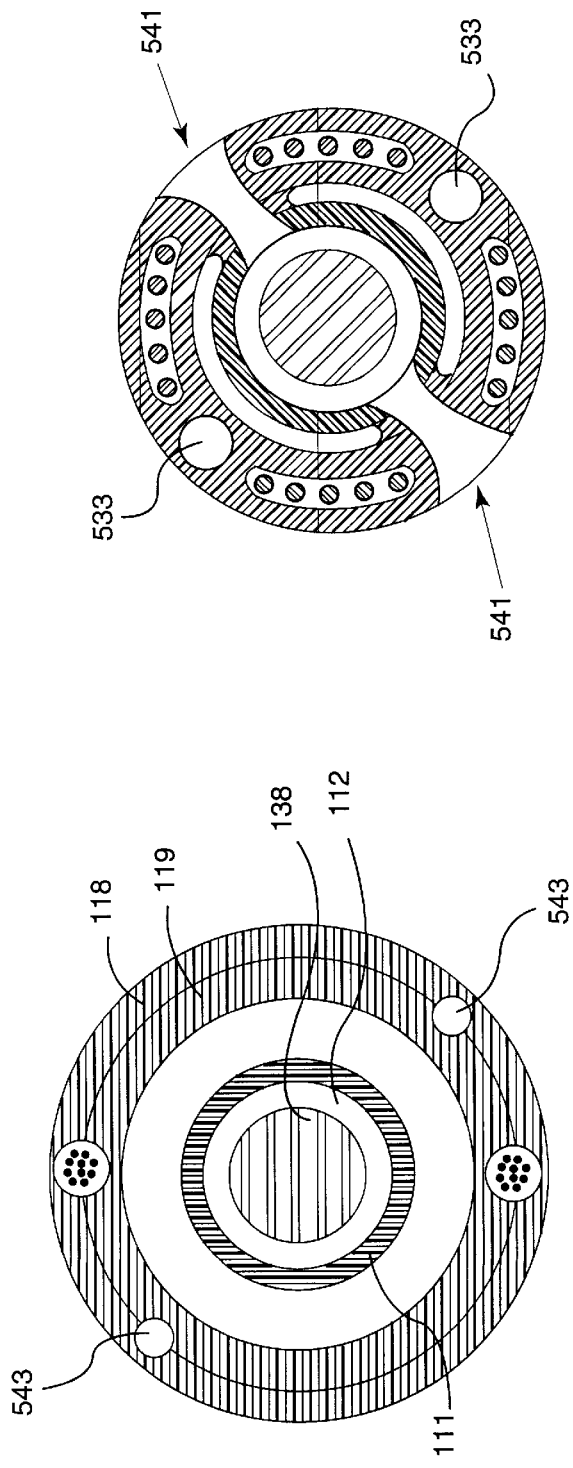

THERMOGRAPHY CATHETER

CROSS-REFERENCE TO RELATED APPLICATIONS

The present application claims the priority of provisional Application No. 60/107,693, filed Nov. 9, 1998 and is a continuation in part of Application No. 08/895,757, filed Jul. 17, 1997, now U.S. Pat No. 5,929,997 which claims the priority of provisional Application No. 60/023,289 filed Jul. 29, 1996, each of which are incorporated herein by reference.

FIELD OF THE INVENTION

The present invention relates generally to medical devices suitable for thermally mapping body vessel segments to locate hot spots (areas with elevated temperatures associated with high metabolic activity) within the vessel. In one particular application, intravascular thermography devices suitable for locating (and in some embodiments treating) vulnerable atherosclerotic plaque in body vessels are described.

BACKGROUND OF THE INVENTION

Cardiovascular disease is one of the leading causes of death worldwide. For example, some recent studies have suggested that plaque rupture may trigger 60 to 70% of fatal myocardial infarctions. In a further 25 to 30% of fatal infarctions, plaque erosion or ulceration is the trigger. Vulnerable plaques are often undetectable using conventional techniques such as angiography. Indeed, the majority of these vulnerable plaques that lead to infarction occur in coronary arteries that appeared normal or only mildly stenotic on angiograms performed prior to the infarction.

Studies into the composition of vulnerable plaque suggest that the presence of inflammatory cells (and particularly a large lipid core with associated inflammatory cells) is the most powerful predictor of ulceration and/or imminent plaque rupture. For example, in plaque erosion, the endothelium beneath the thrombus is replaced by or interspersed with inflammatory cells. Recent literature has suggested that the presence of inflammatory cells within vulnerable plaque and thus the vulnerable plaque itself, might be identifiable by detecting heat associated with the metabolic activity of these inflammatory cells. Specifically, it is generally known that activated inflammatory cells have a heat signature that is slightly above that of connective tissue cells. Accordingly, it is believed that one way to detect whether specific plaque is vulnerable to rupture and/or ulceration is to measure the temperature of the plaque walls of arteries in the region of the plaque.

Once vulnerable plaque is identified, the expectation is that in many cases it may be treated. Since currently there are not satisfactory devices for identifying vulnerable plaque, current treatments tend to be general in nature. For example, low cholesterol diets are often recommended to lower serum cholesterol (i.e. cholesterol in the blood). Other approaches utilize systemic anti-inflammatory drugs such as aspirin and non-steroidal drugs to reduce inflammation and thrombosis. However, it is believed that if vulnerable plaque can be reliably detected, localized treatments may be developed to specifically address the problems.

In view of the foregoing, improved catheters that facilitate the identification, location and mapping of inflamed plaque and/or other hot spots within arteries and/or other vessels would be desirable. Further, integrated catheter devices which are capable of both locating vulnerable plaque and delivering appropriate treatment agents would be desirable.

SUMMARY OF THE INVENTION

To achieve the foregoing and other objects and in accordance with the purpose of the present invention, a variety of improved thermal mapping catheters are disclosed which are capable of sensing and mapping thermal variations within body vessels. In embodiments directed at vascular applications, the catheters are capable of detecting temperature variations in atherosclerotic plaque, on the atherosclerotic plaque surface, and on the arterial wall of aneurysms and other vascular lesions (i.e. arteritis, vasculitis, inflammatory reaction, immunologic reaction, benign growth lesions, and malignant lesions) of the human vasculature.

In one aspect of the invention, a combined thermal mapping and drug delivery catheter is provided. In this embodiment a plurality of thermal sensors are combined with at least one infusion port suitable for delivering therapeutic agents into a vessel. In some embodiments, at least some of the infusion ports are located between adjacent thermal sensors.

In another aspect of the invention, a catheter that includes an expansion device that carries a plurality of the thermal sensors is described. The expansion device is arranged to position the thermal sensors against the walls of a vessel being mapped. In some embodiments, a protective sheath is provided to cover the thermal sensors such that the thermal sensors are positioned between the expansion device and the sheath/member. In a preferred embodiment, the expansion device takes the form of a balloon.

In some embodiments, the expansion device is combined with the infusion ports described above to facilitate localized drug delivery. In some specific implementations the expansion device (e.g. a balloon) is arranged to include a plurality of circumferential recesses in an expanded position in order to place therapeutic agents in physical contact with the vessel wall without being washed away by fluids passing through the vessel.

In some specific implementations, the infusion ports are coupled through a fluid delivery channel in the catheter to a reversible pump that facilitates infusing and/or removing fluids from the vessel. By way of example, these embodiments are particularly useful in applications where it is desirable to pump therapeutic agents (e.g. a radioactive fluid) into a vessel in the region of the thermal sensors and thereafter withdraw the therapeutic agents. Alternatively, separate infusion and withdrawal ports may be provided. In still other embodiments withdrawal ports alone may be provided. The withdrawal ports are particularly useful in applications where it is desirable to withdraw fluid samples (e.g. a blood sample) directly from the region of a vessel being thermally mapped.

In a method aspect of the invention aspect, methods are provided for withdrawing fluid specimens (e.g. blood) directly from in a vessel region of interest (e.g. adjacent vulnerable plaque). In some embodiments, a small vessel segment is isolated for a period of time prior to withdrawing the specimen to permit the infusion of serum markers from surrounding plaque and/or vessel walls. The sample is then taken from the isolated vessel segment.

In another particular method aspect of the invention, a method of treating vulnerable plaque is described. A thermal mapping catheter is inserted into an artery and used to detect the temperature of walls of the artery to identify a region of vulnerable plaque. A radioactive fluid is then applied to the identified region of vulnerable plaque using the catheter to facilitate treatment of the vulnerable plaque. In some embodiments, the radioactive fluid further includes a therapeutic agent. In some embodiments, the radioactive fluid is infused into the distal balloon catheter to deliver the radiation without coming into contact with the bodily fluid.

BRIEF DESCRIPTION OF THE DRAWINGS

The invention, together with further objects and advantages thereof, may best be understood by reference to the following description taken in conjunction with the accompanying drawings in which:

FIGS. 1(a) and 1(b) illustrate a thermal mapping catheter in accordance with one embodiment of the present invention.

FIGS. 2(a)–2(c) illustrate a thermal mapping catheter in accordance with a second embodiment of the present invention.

FIGS. 6(a)–6(c) illustrated another embodiment of a thermal mapping catheter with perfusion capabilities.

FIGS. 7(a)–7(b) illustrate a thermal mapping catheter embodiment that includes drug delivery capabilities.

DETAILED DESCRIPTION OF THE INVENTION

Figure 3A:
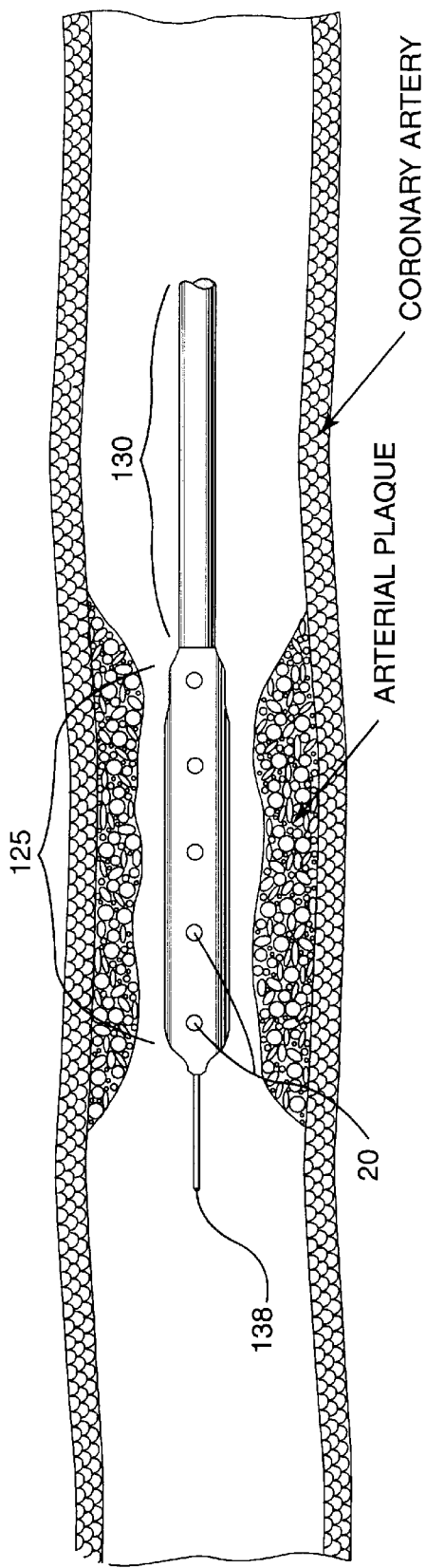
FIG. 3(a) is a side view of the distal end portion of the thermal mapping catheter apparatus of FIG. 2 placed in the vicinity of a lesion in a coronary artery.

Several presently preferred thermal mapping catheter systems and methods of thermally mapping body vessels will be described below making reference to the accompanying drawings. Generally, the described thermal mapping catheters and methods are intended to permit the diagnosis of body vessel regions that have relatively higher heat production compared with surrounding tissues and/or the temperature of adjacent luminal fluid (e.g. blood passing through an artery (vessel) being mapped). In some embodiments, thermal mapping capabilities are combined with other diagnostic or therapeutic capabilities to provide integrated tools for diagnosis and/or treatment of specific conditions. For the purpose of illustration, the inventions will be described in the context of catheters and methods suitable for thermally mapping vulnerable plaque in vascular vessels such as coronary arteries.

Generally, there are a number of considerations that must be addressed when designing a thermal mapping catheter. Initially, although the absolute temperatures of the vessel are of interest, typically there is a greater interest in detecting temperature variation along the vessel. The magnitude of the temperature variations are not large and thus, the thermal sensors used in the catheter must be capable of detecting relatively small temperature variation at or about body temperature. By way of example, the literature suggests that vulnerable plaque and other tissues of interest may have temperature signatures that are on the order of 0.5 to one degree centigrade higher than surrounding tissues or less. In some situations, the temperature variations may be somewhat higher, but it is expected that in most cases, the temperature differential will be less than two to four degrees centigrade. As further research is conducted and additional indicators are identified, it is suspected that even smaller temperature differential may have diagnostic significance.

Referring initially to FIGS. 1(a) & 1(b), one exemplary construction of a catheter apparatus 10 will be described. FIG. 1(a) illustrates a catheter 10 having a multi-lumen elongated flexible tubular member 15 and multiplicity of thermal sensors 20 positioned near its distal tip. The catheter also includes a hub assembly (not shown). The thermal sensors 20 are arranged to detect temperatures at or about body temperature with a very fine resolution. A variety of sensors may be used as the thermal sensors 20, including thermisters, thermocouples, infrared sensing, luminescence absorption and thermal cameras. However, thermisters or thermocouples are utilized in the described embodiment because of their compactness, relatively low cost and simplicity of function. By way of example, Micro Bead thermisters available from Victory Engineering of Springfield, N.J. appear to work well.

In the embodiment shown in FIG. 1, the thermal sensors are arranged in a plurality of longitudinally spaced bands 21, with each band having a plurality of thermal sensors 20. This arrangement permits an elongated segment of vessel to be mapped at one time with good circumferential identification of "hot spots" within the vessel. The longitudinal spacing of the thermal sensor bands 21, as well as the number of sensor bands and sensors per band may be widely varied in accordance with the needs of a particular catheter. For coronary applications longitudinal spacing of the thermal sensor bands 21 in the range of approximately 1 mm to 30 mm apart, and more preferably in the range of approximately 3 to 20 mm, as for example 5 to 10 mm apart would be appropriate. In the described embodiment, the thermal sensor bands are spaced at 10 mm increments and each sensor uniquely measures the temperature at its location. This arrangement has a number of advantages. Specifically, since each sensor uniquely measures the temperature at its location, the temperature signals can be processed and displayed on a monitor in graphical form as diagrammatically illustrated in FIG. 11. The doctor can then readily pinpoint specific vessel segments that have an increased temperature.

The number of rows (i.e. the number of sensors per band) may vary from one to eight or more in accordance with the needs of a particular catheter. In the embodiment shown, four rows of thermal sensors 20, spaced 90 degrees apart around the axis of the flexible tubular member 15 are shown. The number of thermal sensors 20 in each row (i.e. the number of longitudinally spaced sensor bands) may vary from one to twenty or more in accordance with the needs of a particular catheter. However, in the embodiment shown in FIG. 1, there are ten thermal sensor bands 21. This allows the temperatures to be recorded along an extended vessel length.

There are significant tradeoffs in determining the actual number of bands as well as the number of sensors per band for a particular catheter design. Notably thermal sensor cost is likely to be a significant factor in many if not most designs. By way of example, using the Micro Bead thermisters described above, the current costs are likely on the order of $40 per thermister, and thus the costs of the thermisters constitute a very significant percentage of the overall cost of the construction of the catheter. Thus, it will be desirable in many embodiments to reduce the number of thermal sensors used. For example, the cost can be significantly reduced by reducing the number of sensors per band to one or two. However, as the cost of thermal sensors comes down, it may be desirable to provide additional sensors. In the embodiment shown, the sensors are arranged in uniformly spaced rows and bands. However, it should be apparent that the sensors could readily be arranged in a wide variety of patterns, including both non-uniformly spaced and non-aligned patterns.

It is noted that a good thermal map can be made even when each band has only one sensor. The reason for this is that many doctors will be primarily interested in the longitudinal location of a particular hot spot, as opposed to circumferential resolution of the heat distribution at particular longitudinal positions.

As best seen in FIG. 1(b), the flexible tubular member has a plurality of lumens including a guide wire lumen 35 and a plurality of sensor wire lumens 36. Small pinholes are made at appropriate locations along the flexible tubular member 15 and the thermal sensors 20 are attached to the flexible tubular member 15 by feeding the thermal sensor wires 21 through the pin holes. The thermal sensors 20 are then held in place using an appropriate adhesive such as a USP Class VI approved UV cured adhesive such as Dymax® 191-M, 198-M, or a cyanoacrylate adhesive such as those sold by Loctite®. As will be appreciated by those familiar with the construction of thermisters, thermocouples and other thermal sensor, the thermal sensors 20 illustrated in the drawings are diagrammatic in nature and greatly exaggerated in their size as compared to the relative size of most appropriate sensors.

The guide wire lumen 35 is sized appropriately to receive an appropriate guide wire 38 so that the thermal mapping catheter 10 can be inserted into the vascular system using conventional interventional procedures and insertion techniques. More specifically, the moveable guide wire 38 is used to steer the catheter to the desired location in a patient's coronary arterial tree with the aid of angiography. The temperature readings are made when the catheter is appropriately positioned.

Referring next to FIGS. 2(a)–2(c), another embodiment of the invention will be described. In this embodiment, a catheter 110 has a multiplicity of thermal sensors 20 that are mounted on an expandable member 125. In the illustrated embodiment, the expandable member has a compliant dual balloon structure with the thermal sensors being sandwiched (e.g. laminated) between the balloon layers. After the distal tip region of the catheter 110 is inserted into a region of interest, the balloon structure is inflated to place the thermal sensors in contact with the vessel walls. One advantage of this structure is that the thermal sensors can make better and faster temperature measurements of a vessel if they are in contact with the vessel walls since any blood (or other fluid) passing between the vessel being measured and the thermal sensors will interfere at least somewhat with the temperature measurements.

One risk of using a balloon or other expandable device to place the sensors in contact with the vessel is that generally it will be important to insure that the balloon does not significantly stretch the arterial wall when inflated. Current angioplasty balloon and stent delivery systems used in interventional cardiology apply a high inflation pressure to the arterial wall (typically in the range of 6–20 atmospheres). The stretching of the arterial wall in this situation injures the arterial wall. It is well-documented that the injury causes a hyper-proliferative cellular response of the arterial wall and may lead to stenosis or restenosis. Additionally, it is well documented that the application of significant pressure to vulnerable plaque can rupture the plaque and can cause extrusion of plaque content into the blood stream. The plaque content is known to be thrombogenic and can cause acute thrombosis, which is believed to be one of the leading causes of heart attack. Therefore, unlike conventional angioplasty balloons and the like, the positioning balloon 125 is preferably formed from a compliant material that will conform to the topography of the vessel it is measuring and the balloon is inflated using relatively low pressures (as for example, less than ½ an atmosphere above the maximum arterial pressure).

Referring specifically to FIGS. 2(a)–2(c), the catheter 110 has an elongated tubular assembly 130 having a radially expansible laminate balloon 125 carried at its distal end. The elongate tubular assembly 130 includes an inner flexible tubular element 111 that is received within an outer flexible tubular element 115 such that a lumen 116 is formed therebetween. As best seen in FIG. 2(a), the distal end of the balloon 125 is attached to the distal end of the inner flexible tubular element 111, while the proximal end of the balloon 125 is attached to the distal end of the outer flexible tubular member. With this arrangement, the balloon 125 can be inflated by passing fluid through the lumen 116 into the region of the balloon. In the embodiment shown, the inner and outer tubular elements 111 and 115 are independent while in other embodiments they may be integrally formed with appropriate balloon lumens formed such that they open into the region of the balloon.

The laminate balloon structure 125 includes an inner balloon member 119 and an outer balloon member 118. The thermal sensors 20 are mounted between the outer balloon 118 and the inner balloon 119. Like in the previously described embodiment, the spacing and positioning of the thermal sensors 20 may be widely varied in accordance with the needs of a particular catheter. In the embodiment shown, four rows of thermal sensors 20, spaced 90 degrees apart around the axis of the balloon 125 are provided, with, five thermal sensors 20 making up each row.

As best seen in FIGS. 2(a) and 2(c), the outer tubular element 115 has a plurality of elongated lumens 136 that serve as conduits for the thermal sensor wires 21. The wire sensor lumens 136 open into the periphery of the outer tubular element 115 near its distal end. The inner balloon member 119 is attached to the outer tubular element 115 distally of the sensor wire lumen openings, while the outer balloon member 118 is attached to the outer tubular element proximally of the sensor wire lumen openings. With this arrangement, the thermal sensor wires 21 pass between the inner and outer balloon members to connect to the thermal sensors 20. Thus, as best seen in FIG. 2(a), the thermal sensor wires 21 do not penetrate either of the balloon members at any point. Therefore, they do not jeopardize the integrity of the balloon structure 125.

The relative thickness of the inner and outer balloon members may be widely varied to meet the needs of a particular design. In the described embodiment, the inner balloon member 119 is generally thicker than the outer balloon member 118 and is selected to have a lower overall compliance (where compliance is defined as the ratio of change in diameter per change in inflation pressure). With this arrangement, the inner balloon member 119 serves as the primary resistance to inflation. The outer balloon member 118 serves primarily as a protective coating for the thermal sensors and sensor wires 21. Thus, the outer balloon member can readily be fashioned as a sheath that does not attach directly to the flexible tubular members 111 or 115 or as a coating material that encapsulates the thermal sensor wires. However, when attached as a second balloon, the outer balloon member 118 serves as a backup balloon in the event that the first balloon member fails. As pointed out above, in some embodiments, the outer balloon member 118 may be thinner and to be more compliant than the inner balloon member 119. Generally, the thinner the outer balloon member 118, the better the thermal conductivity will be between the thermal sensors 20 and the vessel wall. Although in the described embodiment, the inner balloon member is thicker and less compliant than the outer balloon, it should be appreciated that this is by no means a requirement for all embodiments and the relative thickness and compliance of the balloon members may be widely varied.

As pointed out above, in most embodiments, one important feature of the positioning balloon structure 125 is that unlike conventional angioplasty balloons the positioning balloon 125 is preferably formed from a very compliant (or at least semicompliant) material that will gently conform to the topography of the vessel it is measuring. The balloon is inflated using relatively low pressures as for example, in the range of approximately ¼ to 1 atmosphere of pressure and preferable less than ½ an atmosphere above the maximum arterial pressure. The intent of the positioning balloon structure 125 is to place the thermal sensors in contact with (or at least closer to) the vessel walls without significantly stretching or injuring or pressing strongly against the vessel during the thermal sensing. It should be appreciated that this approach is much different than the approach used in conventional balloon based coronary procedures such as angioplasty.

The inner and outer balloon members 118, 119 can be made from one of the many available thermoplastic elastomers (TPE). Manufacturers of these TPE's include but are not limited to, Dow Chemical, Concept Polymer Technologies, Inc., CT Biomaterials, and Colorite Polymers. Although the above listed polymers tend to be of a compliant nature, it will become obvious to those skilled in the art that other less compliant polymers can be used and may vary in accordance with the needs of a particular catheter.

In the embodiment seen in FIGS. 2(a)–2(c), the inner flexible tubular element 111 has a single central lumen 112, which serves as a guide wire lumen. The thermal mapping catheter can thus be inserted into the appropriate location in a patient's coronary arteries or other vessels using an "over the wire" insertion technique. In embodiments where it is desirable to combine the thermal mapping catheter with ultrasonic imaging, the guide wire lumen 112 of the inner flexible tubular element 111 can be sized to accept a guide wire 138 with imaging capability (not shown) as described, for example, in Pomeranz, U.S. Pat. No. 5,558,093 which is incorporated herein by reference.

Radiopaque marker bands 113 may be attached to the periphery of the inner flexible tubular element 111 using any suitable technique. The radiopaque marker bands 113 are positioned on the inner flexible tubular element 111 so that the thermal sensors 20 are located between the two marker bands. In the illustrated embodiment, the radiopaque marker bands 113 are attached to the outside diameter of the inner flexible tubular element 11 by mechanical crimp or adhesive bonds. As will be appreciated by those familiar with interventional techniques, the purpose of the marker bands is to make the catheter tip more visible using angiography to show the physician the relative location of the thermal sensors 20 in relation to the vessel area being mapped.

Figure 3B:
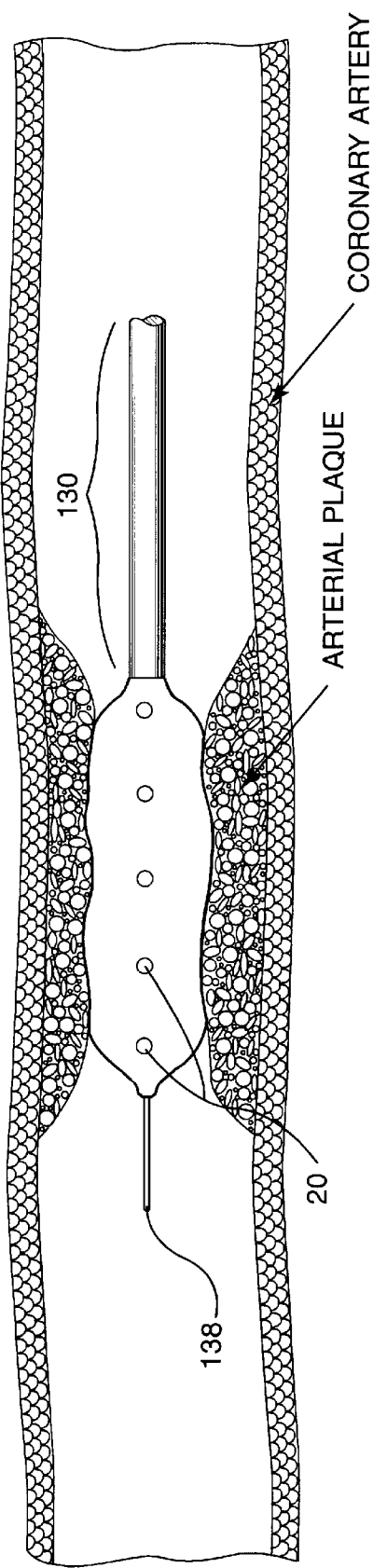
FIG. 3(b) is a side view of the distal end portion of the thermal mapping catheter apparatus of FIG. 3(a) placed in the lesion of a coronary artery with the laminate sensing balloon expanded to record plaque temperatures.

To thermally map a particular portion of an artery, the thermal mapping catheter may be inserted to an appropriate location using normal interventional procedures and techniques. A moveable guide wire 138 is used to steer the catheter to the desired location within the vasculature with the aid of angiography. The catheter is positioned as illustrated in FIG. 3(a) where the catheter tip has been positioned adjacent a vascular lesion to be mapped. The radially expansible balloon arrangement 125 is then conformally inflated so that the thermal sensors 20 contact the artery walls (e.g. the vascular lesion) as illustrated in FIG. 3(b). The inflated balloon substantially stops the flow of blood through the artery and thus, the blood flow does not interfere with the temperature measurements. Since the thermal sensors are in contact or close proximity to the vessel walls the temperature readings can be made very quickly and thus the balloons can be deflated shortly after it is inflated to restore the flow of blood through the artery. As will be appreciated by those skilled in the art, in various coronary procedures such as stenting and angioplasty, it is not uncommon to occlude the flow of blood through an artery for on the order of 45 seconds to a minute and this is not seen as being dangerous to the patient. Suitable temperature readings can readily be made in much less then 45 seconds and thus, the temporary occlusion of vessel should not be a problem. After a temperature reading has been made, the balloon arrangement 125 is deflated and the catheter tip may be repositioned to take a new reading. Thus, if an extended section of artery is to be mapped, the catheter may be repeatedly positioned for a reading and then advanced to the next position, with the balloon structure being repeatedly inflated and deflated at each position to take the appropriate temperature readings.

It should be apparent that generally, it will be desirable to reduce the number of inflation/deflation cycles that will be required to map a particular vessel region. Therefore, in thermal mapping catheters that are intended for use in mapping extended vessel lengths, it may be desirable to utilize relatively long and/or multiple balloon structures and to provide a relatively large number of longitudinally spaced sensors. By way of example, balloon lengths on the order of 2 to 15 cm and longer are appropriate for many applications. To keep the costs of the thermal sensors reasonable, in many applications it may be desirable to reduce the number of thermal sensors in each sensor band to one or two. Although this may reduce the circumferential sensitivity of the mapping catheter, in many situations this level of sensitivity will work fine. For example, in many situations the most important issue is the longitudinal location of vulnerable plaque along the coronary tree as opposed to its circumferential position within the vessel. In other situation, the plaque of interest may be known to be on a particular side of the vessel and thus only that general portion of the vessel needs to be mapped.

Although a particular embodiment of the positionable thermal sensors has been described above with respect to FIG. 2, it should be appreciated that the design may be widely varied. The elongate tubular assembly 130 may be formed in a variety of ways and the lumens therein may be extruded in any of a variety of configurations and shapes in accordance with the needs of a particular catheter.

As will be described in more detail below, one application of the described catheter is to deliver radiation to the region of diagnosed vulnerable plaque to facilitate treatment of the plaque. In some applications it may be desirable not to release radioactive materials into the bloodstream. In such applications, a radioactive fluid can be used to inflate the balloon, thereby delivering radiation to the vulnerable plaque. The described dual balloon structure (and particularly the thinner outer and thicker inner balloons) is quite well suited for such applications since it provides additional safety in the event that one of the balloons is breached.

In applications where radioactive fluids are used, it may also be desirable to have separate inflation and deflation lumens so that the radioactive fluid can be removed from the catheter after the desired exposure period. By way of example, this can be readily accomplished by dividing lumen 116 into two segments.

Figure 4A:
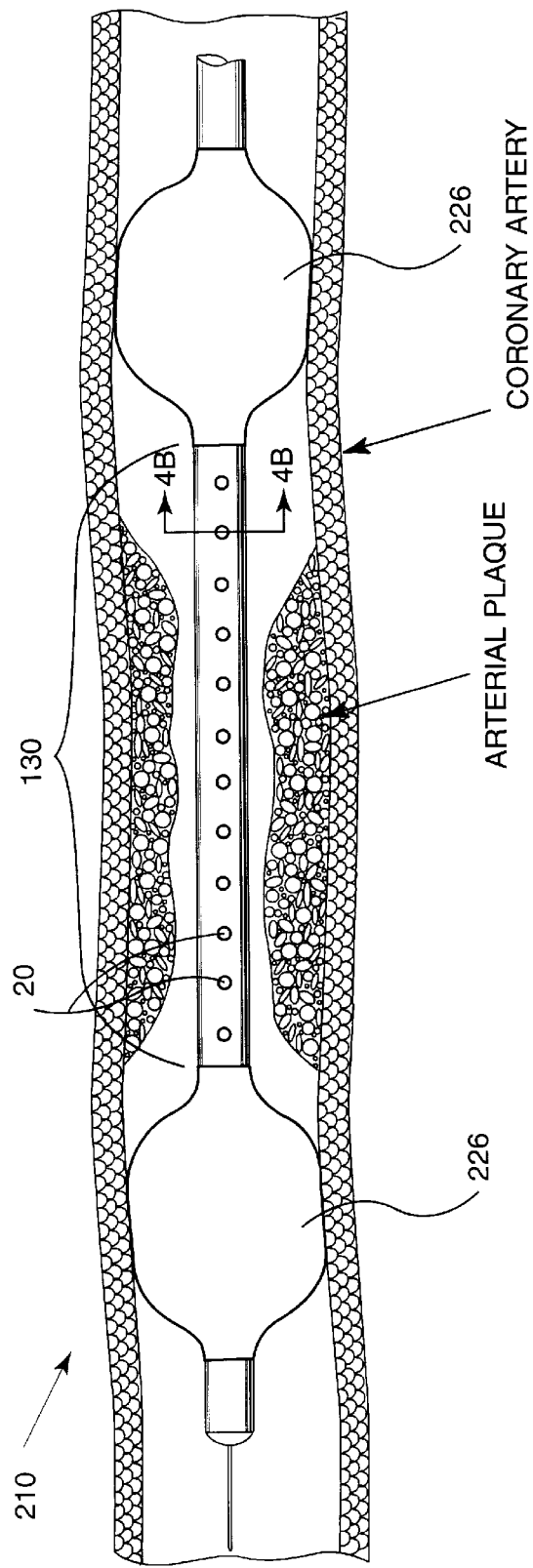
FIGS. 4(a)–4(b) illustrate a thermal mapping catheter in accordance with a third embodiment of the present invention.
Figure 4B:
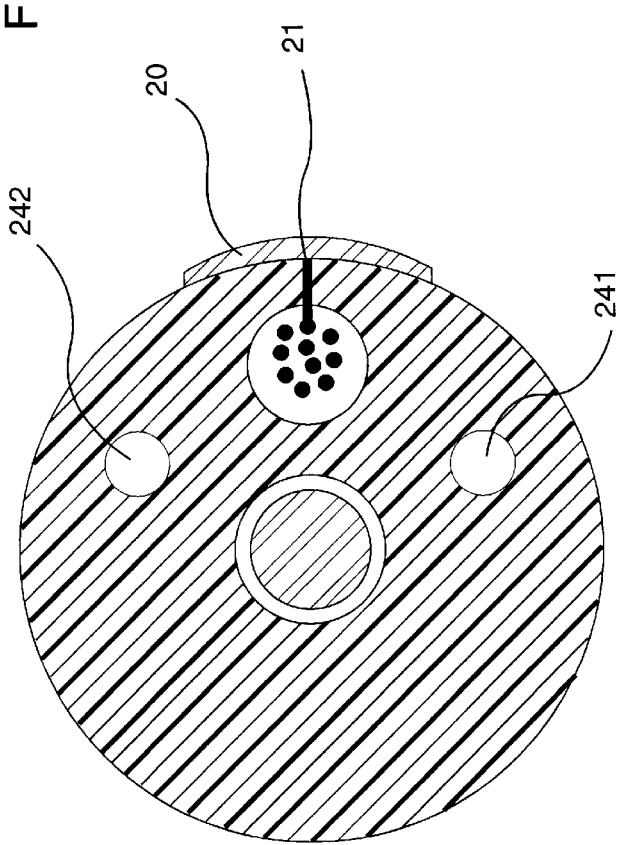

Referring next to FIGS. 4(a) and 4(b), yet another catheter embodiment will be described. In this embodiment, the influence of the blood on the sensors is addressed in another way. The catheter 210 includes a pair of occlusion balloons 226 on opposite (i.e. proximal and distal) ends of the thermal sensor array. The purpose of the occlusion balloons 226 is to temporarily stop the flow of blood through the vessel during the thermal sensing. In the illustrated embodiment, the thermal sensors are not purposefully placed in contact with the vessel wall. Rather the thermal mapping catheter 210 is positioned with the occlusion balloons straddling the vulnerable plaque or other region of interest. The occlusion balloons 226 are then inflated thereby blocking the flow of blood over the thermal sensors 20. Although a pool of blood remains around the thermal sensors 20, the pool of blood is relatively static (although the beating heart will cause some movement and agitation) and it is still possible to make sufficient readings of the vessel temperature since heat from "hot spots" in the vessel walls will tend to warm the nearby blood faster than the surrounding regions.

The amount of time that the occlusion balloons are inflated will be a function of several factors. Generally, in coronary procedures such as stenting and angioplasty it is common to occlude the flow of blood for on the order of 45 seconds to one minute during the procedure. Such a period of occlusion is believed to be sufficient to make high quality thermal mapping readings in most applications. It should be apparent that the occlusion approach of FIG. 4 is generally not able to make temperature measurements as quickly as direct contact approaches (such as illustrated in FIG. 2). However, in circumstances where the location of the target plaque is generally known and can be straddled it avoids the perceived risks of a balloon pressing against the vessel walls. The occlusion approach also generally lends itself towards faster and better readings than approaches that permit the flow of blood between the thermal sensors and the vessel wall (such as illustrated in FIG. 1).

With the catheter illustrated in FIG. 1, it should be appreciated that blood continues to flow past the thermal sensors while the temperature measurements are being made. One drawback of this approach it inherently somewhat less sensitive to small temperature variations and therefore will generally be somewhat slower than approaches which stop the flow of blood or place the sensors in direct contact with the vessel walls. However, at the same time it avoids the perceived risks of a balloon or other expansion device pressing against the vessel walls.

In the embodiment shown in FIG. 4, a single sensor is used for each longitudinally spaced thermal sensor band 220. As suggested above, and as will be apparent from the discussion of combined thermal mapping and drug delivery catheters below, in many situations the most important information is the longitudinal location of the vulnerable plaque and its circumferential position within the vessel, while interesting, is not as important.

Figure 11:
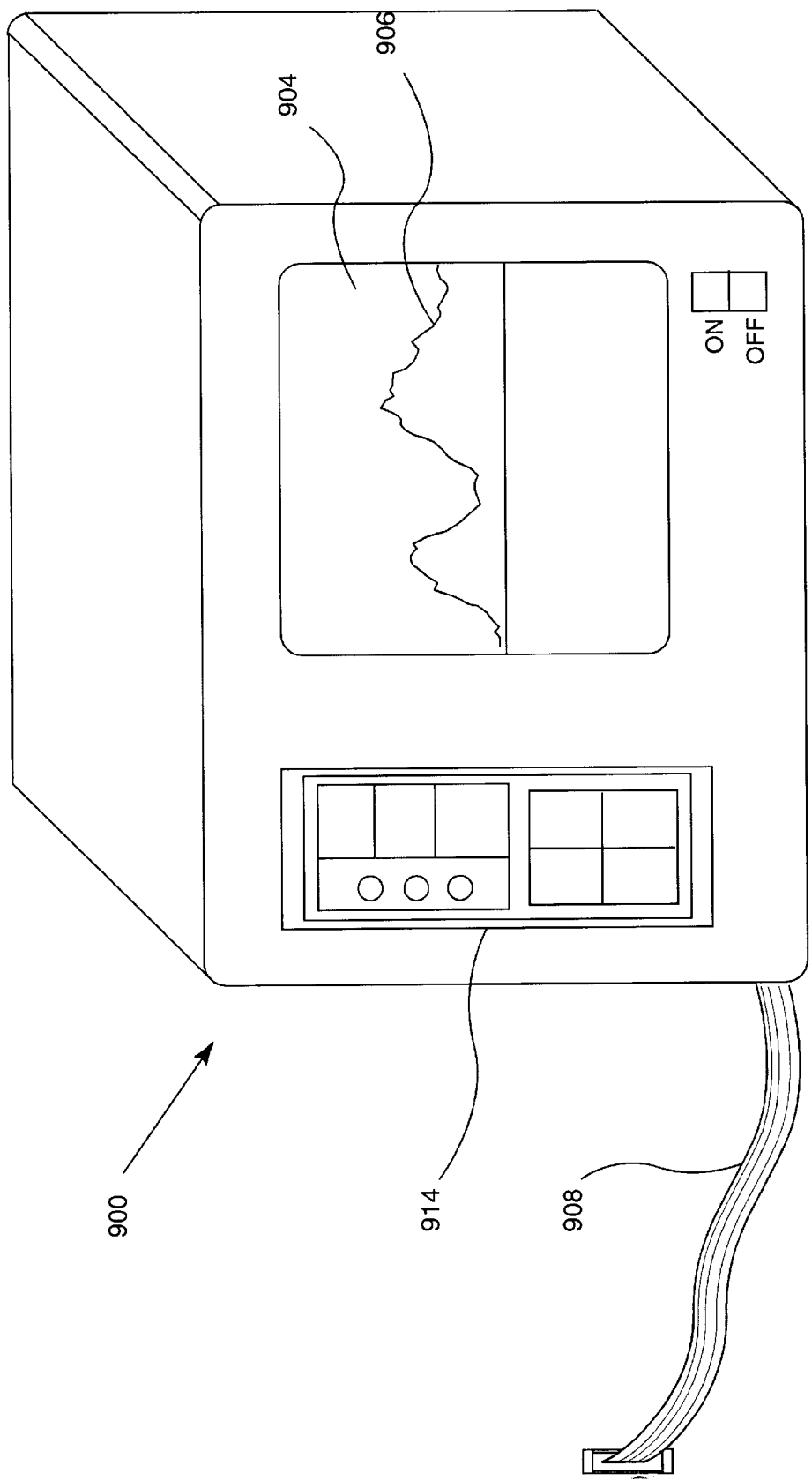
FIG. 11 is a diagrammatic representation of a monitor having a screen displaying a thermal map taken using one of the described thermal mapping catheters.

As described above, for coronary applications, longitudinal spacing of the thermal sensor bands in the range of approximately 1 mm to 30 mm apart, and more preferably in the range of approximately 3 to 20 mm, as for example 5 to 10 mm apart is appropriate. Since each sensor uniquely measures the temperature at its location, the temperature signals can be processed and displayed on a monitor in graphical form (such as shown in FIG. 11) thereby allowing the doctor to readily pinpoint specific vessel segments that have an increased temperature.

Like the previously described embodiments, the flexible tubular member 230 used in catheter 210 may be formed in a wide variety of ways. By way of example, a multi-lumen structure that includes a guide wire lumen, a pair of inflation lumens, and one or more sensor wire lumens as illustrated in FIG. 4(b) works well. The inflation lumens 241, 242 connect to respective occlusion balloons 226 and are arranged to deliver the fluid used to inflate the occlusion balloons. Like the previously described embodiments, the catheter 210 may be inserted and positioned using normal interventional procedures and techniques. In the embodiment shown, each balloon is fed through an independent inflation lumen. This permits independent control of the inflation of the two balloons. When independent control of the occlusion balloons is not considered important, then a single inflation lumen may be used.

In the embodiments described above with respect to FIGS. 2 and 4, balloons have been described that effectively occlude the flow of blood through the vessel when inflated. Generally it is expected that the balloons would be inflated during thermal sensing and then deflated to restore the flow of blood through the vessel. However, in some circumstances it may be desirable to maintain the flow of blood through the vessel while the balloons are inflated and/or temperature measurements are being made. One good example of this is when the thermal mapping catheter is combined with drug delivery systems (as will be described in more detail below). In such situations it may be desirable to keep the balloons inflated for an extended period to localize the delivery of therapeutic agents. It may be unsafe to occlude the flow of blood for that period of time and thus it may be desirable to provide the catheter with perfusion capabilities so that the flow of blood may continue during use of the catheter.

Figure 5A:
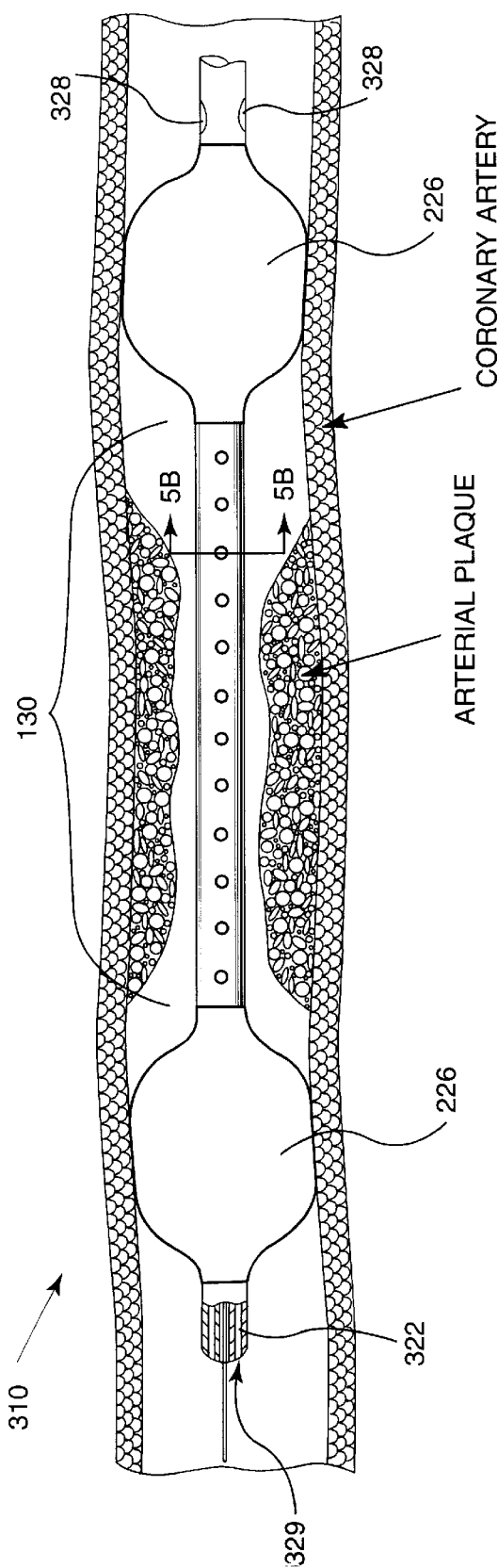
FIGS. 5(a)–5(b) is a cross sectional view of the distal portion of a thermal mapping catheter apparatus incorporating the laminate balloon and perfusion aspects of the present invention.
Figure 5B:
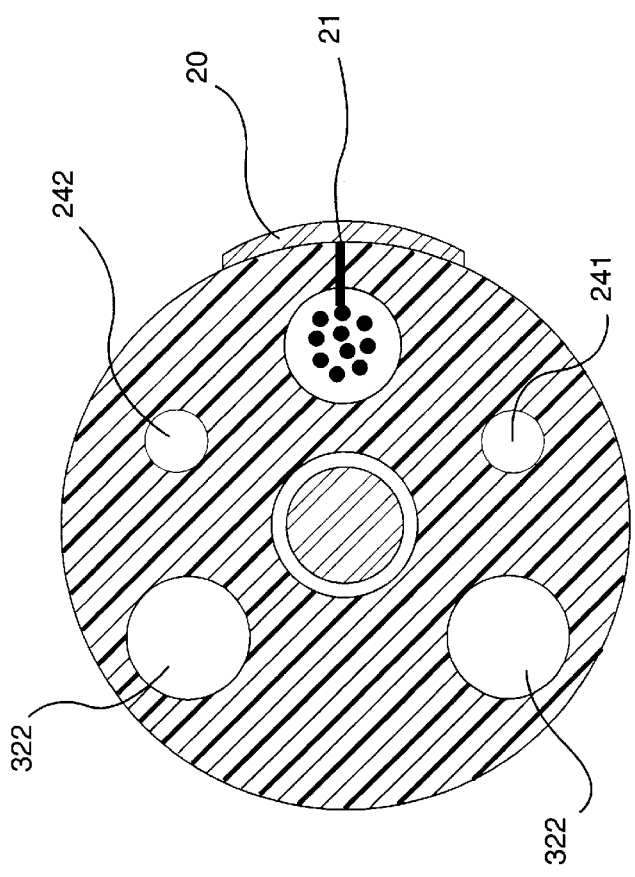

Referring next to FIGS. 5(a) and 5(b), a catheter 310 that combines thermal mapping with perfusion capabilities will be described. Like in the previously described embodiments, the actual construction of catheter 310 may be widely varied. In the embodiment shown, the catheter 310 is quite similar to the catheter 210 having a pair of occlusion balloons 226 as described above with respect to FIG. 4. The flexible tubular member 330 is similar to the elongated tubular assembly described above with respect to FIG. 4, but it also includes a plurality of perfusion conduits 322 that extend from proximal ports 328 that open proximally of the proximal occlusion balloon 226 to distal ports 329 that open at the distal tip of the catheter. When the occlusion balloons 226 are inflated potentially occluding the vessel, blood flowing through the vessel enters the perfusion conduits 322 through one set of ports and exits through the other thereby permitting continuous flow of blood through the vessel.

In some embodiments the perfusion conduits may be combined with lumens that serve other functions. For example, the ports may open into the guide wire lumen to allow the guide wire lumen to serve as the perfusion conduits. The number of fluid delivery conduits 322 used in a particular catheter design may widely vary in accordance with the needs of a particular implementation. By way of example, on the order of one to four conduits would be typical although additional conduits (as for example eight or more) could be provided. In the illustrated embodiment, a pair of perfusion conduits are provided in the flexible tubular element 330. In the embodiment shown, the perfusion conduits are isolated from the thermal sensor wires to minimize the effect of the flowing blood on the temperature measurements.

Referring next to FIGS. 6(a)–6(c) another embodiment of a thermal mapping catheter with perfusion capabilities will be described. In this embodiment, the catheter 410 is quite similar to the catheter 110 having a balloon based sensor positioning arrangement 125 as described above with respect to FIG. 2. The flexible tubular member 430 is similar to the elongated tubular assembly described above with respect to FIG. 2, but it also includes a plurality of perfusion conduits 422 that pass through the inner flexible tubular member 111. The perfusion conduits 422 extend from proximal ports 428 that open proximally of the sensor positioning balloon arrangement 125 to distal ports 429 that open at the distal tip of the catheter. When the sensor positioning balloon 226 is inflated potentially occluding the vessel, blood flowing through the vessel enters the perfusion conduits 422 through one set of ports and exits through the other thereby permitting continuous flow of blood through the vessel. As previously described, in some embodiments the perfusion conduits may be combined with lumens that serve other functions such as the guide wire lumen. For example, the ports may open into the guide wire lumen to allow the guide wire lumen to serve as the perfusion conduits.

It should be appreciated that almost any thermal mapping catheter design can be provided with perfusion capabilities. In operation, the catheters of FIGS. 5 and 6 would operate similarly to the catheters described above. When the balloons are inflated, blood enters through the ports located on one end of the perfusion conduits (e.g. the proximal ports) and exits through the other ports (e.g. the distal ports).

The thermal mapping catheter embodiments that have been described above are essentially diagnostic tools that may be used to thermally map vessel segments. In many cases it is expected that thermal mapping is all that would be desired. However, in many situations, thermal mapping alone will not be sufficient. Rather, it will be desirable to combine thermal mapping capabilities with other diagnostic and/or therapeutic capabilities to provide integrated catheter devices. Indeed in today's managed health care environment, it is often difficult to persuade insurers to reimburse the costs of purely diagnostic intravascular procedures. Therefore, in the long term it is expected that most devices that utilize thermal mapping will be combination devices that have other capabilities as well. By way of example, combination thermal mapping and drug delivery devices permit a physician to both diagnose and treat vulnerable plaque in one procedure. Similarly, integrated thermal mapping and ultrasonic imaging devices permit more complete diagnosis of specific regions.

Referring next to FIGS. 7(a)–7(b), a catheter 510 that combines thermal mapping with drug delivery capabilities will be described. Like in the previously described embodiments, the actual construction of catheter 510 may be widely varied. In the embodiment shown, the catheter 510 is quite similar to the catheter 110 having a thermal sensor positioning balloon 125 as described above with respect to FIGS. 2 and 6. The elongated tubular assembly 530 is similar to the elongated tubular assembly described above with respect to FIG. 2, but the outer tubular member 515 also includes a plurality of fluid delivery conduits 533 that are coupled into infusion ports 541 located within the balloon structure through small tubes 543. Therapeutic or diagnostic agent can be delivered to a region of interest by introducing the agents into the vessel through the infusion ports 541. Similarly, blood samples in the region of a lesion may be taken by withdrawing blood through the infusion ports. In some embodiments the fluid delivery conduits may serve multiple functions. For example, they may be combined with the guide wire lumen or a sensor wire lumen, etc. to serve multiple purposes. The number of fluid delivery conduits 533 used in a particular catheter design may widely vary in accordance with the needs of a particular implementation. By way of example, on the order of one to four conduits would be typical although additional conduits (as for example eight or more) could be provided. In the illustrated embodiment, a pair of fluid delivery conduits are provided that are spaced at 180 degree increments about the axis of the outer flexible tubular element 515.

In the embodiment shown, the infusion ports 541 are located between and adjacent the thermal sensors. This has several advantages. For example, when therapeutic agents are infused, they can be delivered directly to an area that was just mapped without requiring repositioning of the catheter.

The fluid delivery conduits may be formed in any suitable manner. In the embodiment shown, the portions of the fluid delivery conduits within the outer tubular member 515 are simply extruded lumens which open into the distal end of the outer tubular member 515. Small tubes 543 pass between the inner and outer balloon members 119, 118 and are used to couple the fluid delivery lumens to the infusion ports 541. Thus, the infusion ports 541 only penetrate the outer balloon member 118. Since the infusion ports do not pass through the inner balloon member 119, the integrity of the balloon structure 125 is not compromised. The tubes 543, may be formed from any suitable material such as polyurethane. The tubes may be coupled to the outer tubular member 515 by any suitable process. By way of example, a tubes 543 may be thermally attached to the distal end of the outer tubular member 515 at appropriate locations over the fluid delivery conduits 533. The infusion ports may be made simply by poking holes at appropriate locations along the tubes 543 as best illustrated in FIG. 7(a). By thermally bonding the tubes 543 to the outer balloon member 118 in the regions of the infusion ports, fluid can be prevented from entering the space between the inner and outer balloon members 118, 119.

Figure 8:
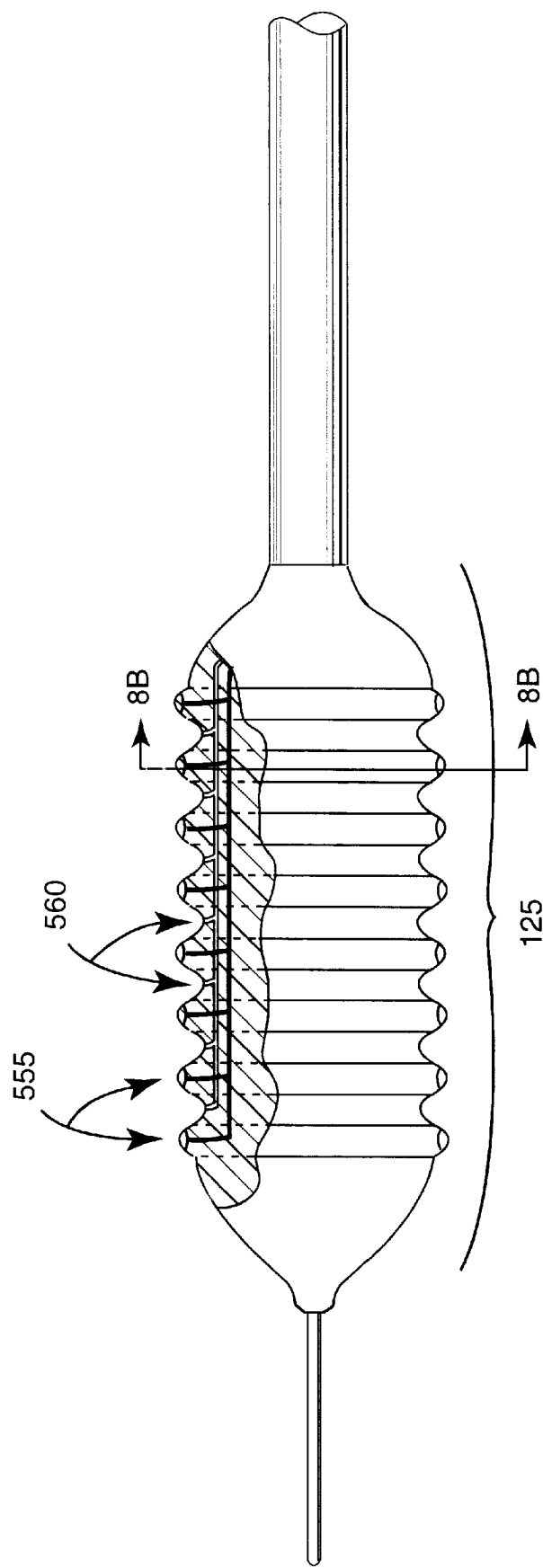
FIG. 8 is a side view of the distal end portion of the thermal mapping catheter apparatus of FIG. 7 placed in the vicinity of a lesion in a coronary artery.

In order to improve the localization of the delivery a therapeutic agents, the balloon structure may have a ribbed or convoluted configuration (somewhat like a flexible hose structure in appearance), with the thermal sensors being positioned on the peaks of the convolutions 555 and the infusion ports being positioned in the valleys of the convolutions 560. This structure is best illustrated in FIG. 8 which shows an balloon in an inflated position. The annular valleys 560 permit the therapeutic agents to pool in the region immediately adjacent the thermal sensor, which facilitates the direct application of therapeutic agents to vulnerable plaque or other lesions or vessel segments of interest. That is, they place the therapeutic agent in physical contact with the vessel wall without being washed away by blood or other fluid within the vessel. Of course if it is not desirable to effectively hold the therapeutic agents against the vessel for a period of time, the agents can be infused with the balloon in the deflated or a partially inflated position.

The ribbed pattern may be formed in the balloon structure during its fabrication using any suitable technique. By way of example, the ribs may be formed by expanding the balloon tubing in a pre-machined two piece aluminum mold or heat shrinking the balloon over 0-rings or a wide variety of other processes. As discussed above, the balloon structure 125 is intended to be compliant. Therefore, the infused therapeutic agents are entrapped somewhat in place by the valleys in the convolutions and will have sufficient time to infuse into the vessel wall or plaque.

Figure 9A:
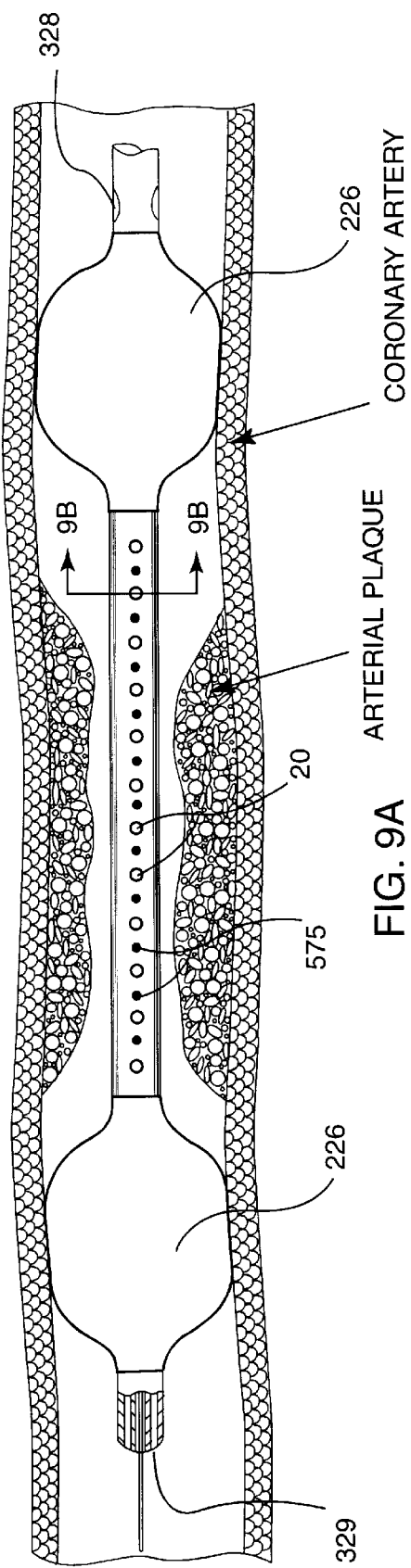
FIGS. 9(a)–9(b) illustrate another embodiment of a thermal mapping catheter embodiment that includes drug delivery capabilities.
Figure 9B:
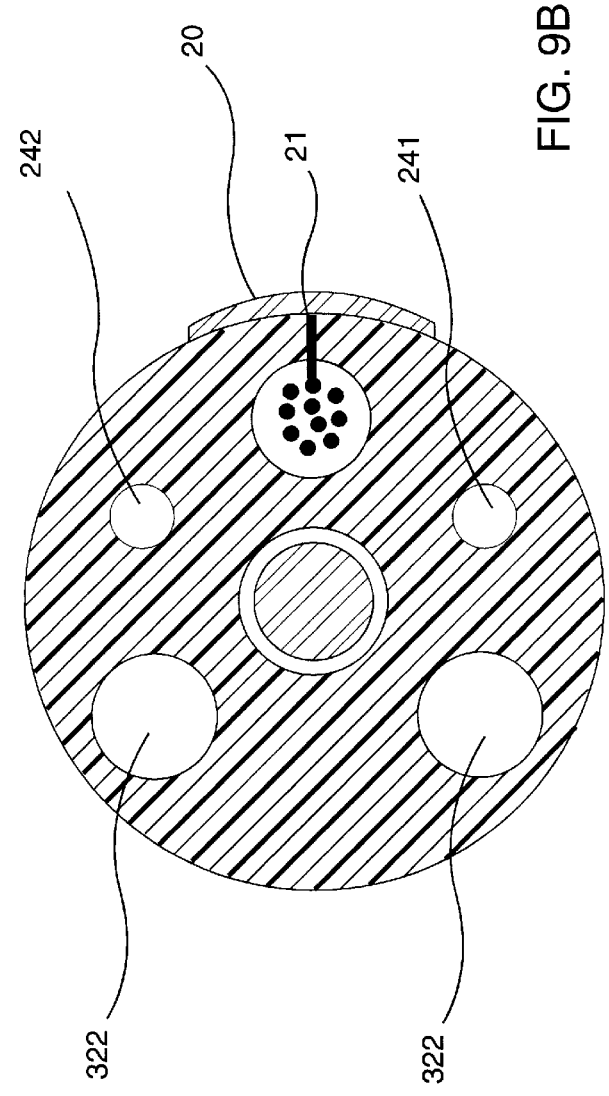

Referring next to FIG. 9, yet another thermal mapping catheter embodiment will be described. This embodiment adds infusion ports, but is otherwise substantially similar to the pair of spaced occlusion balloons embodiment of FIG. 5(a). As in the previously described infusion port embodiment, the infusion ports 575 are placed between and/or relatively closely to the thermal sensors 20. In order to carefully control the amount of drug or other agents delivered to a specific site, the occlusion balloons 226 may be inflated thereby isolating a region of the vessel. Infusion of the agents into that isolated region allows the agents to be delivered directly to the desired region. With the use of a reversible pump, the infusion ports may also be used to withdraw the agent after it has been infused in circumstances where withdrawal of the agent is deemed desirable. For example, as described in more detail below, when a radioactive fluid or diagnostic agent is use, it may be desirable to withdraw the agent before deflating the occlusion balloons.

The described infusion port structure can readily be modified to facilitate the withdrawal of samples from the vessel. Again, this can be accomplished in a number of ways. In some embodiments, fluid withdrawal is accomplished by simply using a reversible pump to infuse and withdraw fluids through the infusion ports and fluid delivery conduits. Alternatively, separate infusion and withdrawal ports may be provided, with separate pumps to accomplish specific tasks. The described structure provides a good tool for taking serum or other samples directly from regions of a vessel that are identified as being at risk. Such localized samples have powerful diagnostic potential that is unattainable using current technology.

By way of example, a small blood sample taken in the vicinity of vulnerable plaque will include a number of serum markers associated with the vulnerable plaque which may be used to diagnose or further diagnose the plaque. For example, the serum markers may include inflammatory markers (e.g., TNF, interleukins, etc.), tissue factors, enzymatic biologics (i.e., proteinases), cytokines (e.g., interleukins and interferon), and/or blood inflammatory cells (e.g. macrophages, neutrophils).

Samples may be taken from any of the described infusion devices. However, it should be apparent that the occlusion balloon style catheter is particularly well suited for many such applications since when the occlusion balloons are both inflated, a small arterial segment is isolated and compartmentalized. The arterial segment can be isolated for sufficient time to permit biochemical markers to infuse from the surrounding vessel, plaque, etc. into the blood which is then drawn as a sample. For example, by isolating a region of the vessel adjacent to vulnerable plaque, various biochemical markers will infuse from the vulnerable plaque into the blood sample. Indeed, vulnerable plaque is known to generate a significant amount of biochemical markers. In many situation, those markers will provide much more useful diagnostic information than would be possible using conventional diagnostic testing.

As mentioned above, in some applications it will be desirable to provide an integrated mapping tool that facilitates both thermal mapping and vessel imaging functions, since these techniques provide different (and potentially complimentary) information about the vessel. There are currently a variety of imaging technologies available, including ultrasonic imaging catheters, angioscopy catheters and angiography catheters and it may be desirable to include any of these with thermal mapping. The thermal mapping identifies metabolic hot spots but is not well adapted to show the luminal size of a vessel or lesion. In contrast, for example, ultrasonic imaging is well suited to illustrate the structure of plaque, but is not able to distinguish dangerous plaque from ordinary plaque. Thus, the attraction of integrated devices. One simple way to provide an integrated thermal mapping and ultrasonic imaging catheter is to provide a relatively large guide wire lumen in any of the described catheters. A conventional ultrasonic imaging catheter can then effectively be used as the guide wire for the thermal mapping catheter. By way of example, an ultrasound catheter such as that described by Yock, U.S. Pat. No. 4,794,931, No. 5,000,185, and No. 5,313,949 or that described by Maroney et al, U.S. Pat. No. 5,373,849 each of which are incorporated herein by reference would work well.

The earlier referenced U.S. patent application Ser. No. 08/895,757, describes other integrated catheter approaches as well. In other applications it may be desirable to provide stent or patch delivery capabilities together with the thermal mapping. For example, once vulnerable plaque is identified, it may be desirable to apply a stent or a patch to a diseased region of the vessel.

A few specific mapping catheter designs have been described above. These catheters can be used in a variety of treatments that are not possible using conventional techniques. As pointed out in the background section, there are currently no devices available on the market that can identify vulnerable plaque in vascular vessels. Thus, current treatments for vulnerable plaque are very general in nature. That is most medications are taken either orally or intravenously. However, while these approaches have had some success, it is believed that delivering medications directly to the vicinity of vulnerable plaque will in many circumstances significantly improve the efficacy of treatment and result in faster therapeutic effects.

The described thermal mapping catheters can be used to identify vulnerable plaque. Integrated thermal mapping/drug delivery catheters provide the ability to first diagnose dangerous plaque and then seek to treat it immediately using the same device. The types of agents used may be both therapeutic and diagnostic in nature. For example, anti-inflammatory agents may be delivered directly to the area of inflamed plaque to decrease the inflammation associated with vulnerable plaque. Anti-thrombotic agents may be delivered to the region to reduce the risk of thrombosis during a particular procedure. Low dose radiation may be delivered to the inflamed region of the plaque to kill inflammatory cells. In other applications antibodies may be delivered to the area of vulnerable plaque for either therapeutic or diagnostic reasons.

As pointed out above, vulnerable plaque tends to have a number of inflammatory cells. In other applications such as treatment of coronary restenosis, radiation has been used successfully to reduce proliferation of connective tissue cells. It is believed that radiation can be used to reduce the inflammation within vulnerable plaque. At the time of this writing, the applicants are unaware of any literature that suggests the use of radiation to reduce such inflammation. However, the effect of radiation on inflammatory cells in general is well-documented.

The described infusion catheters can be used to inject a radioactive fluid directly into a vessel with vulnerable plaque to reduce the number of inflammatory cells such as macrophages and neutrophils in the region of the plaque. Reducing the number of inflammatory cells reduces inflammation, which in turn reduces the vulnerability of the plaque. By way of example, using the occlusion balloon based infusion catheter described above with reference to FIG. 9, once vulnerable plaque has been identified, a radioactive fluid can be injected through infusion ports 575 directly into the region between occlusion balloons 226. With this arrangement, the occlusion balloons hold the radioactive fluid in place where it needed and the dosages can be controlled quite well.

A variety of materials may be used as the radiation fluid. By way of example, the radiation fluid may include: radionucleotides such as heparin bound P-32, H-3, and Y-90 for beta-isotopes; antibodies bound with isotopes such as metaloproteinase; antibody-bound beta isotopes such as P-32; or gamma isotopes such as I-125 or I-131. These isotopes will provide doses in the range of 2–20 Gy at a depth of 3 mm from the endothelium. Preferably, the isotopes will deliver a total dose in the range of approximately 2–10 Gy at the prescribed depth. The actual radiation dosages and exposure periods that are appropriate for different lesions may vary widely in accordance with a particular treatment schedule.

After the appropriate level of radiation has been applied, the radioactive fluid may either be released (to be filtered by the kidneys) by deflating the occlusion balloons 226, or a pump may be used to withdraw the radioactive fluid from the vessel through the infusion ports 575. The radioactive fluid may be withdrawn either while both occlusion balloons are inflated, or while the upstream occlusion balloon is at least partially deflated to allow additional blood to flow into the isolated region. In many applications where the use of radiation is contemplated, it will be preferable to provide the catheter with perfusion capabilities since it will often be desirable to apply radiation for time periods that are longer then the vessel can be safely occluded.

In some applications it may be deemed undesirable to infuse radioactive fluid into the vessel (e.g. bloodstream). The expansion balloon based catheter previously described with respect to FIGS. 2, 6 and 7 is well suited for this application. Specifically, a radioactive fluid may be used in place of the saline used to inflate the balloon when radiation exposure is desired (as for example by adding radioactive isotopes such as I-125 or I-131 to the saline solution). As pointed out above, the described dual balloon structure is quite well suited for such applications since it provides additional safety in the event that one of the balloons is breached.

In one method, an expansion balloon based catheter may be placed within a coronary artery and the balloon expanded using a normal saline solution to facilitate thermal mapping. If the thermal mapping identifies vulnerable plaque, the saline solution can be withdrawn thereby deflating the laminate balloon structure 125. A radioactive fluid may then be used to expand the balloon. In the expanded configuration, the radioactive fluid is contained within the balloon, thereby preventing its leakage into the bloodstream, however the vessel walls are exposed to radiation. The balloon is kept expanded for the period of time deemed appropriate to treat the vessel.

The actual radiation dosages and exposure periods that are appropriate for different lesions may vary widely in accordance with a particular treatment schedule. By way of example, as pointed out above, dosages of less than about 10 Gy of gamma or Beta radiation at the prescribed depth are generally appropriate. Of course, if the radiation exposure period is longer than a minute or so, it will be desirable to use a catheter with perfusion capabilities as previously described.

To facilitate the separate delivery of saline and radioactive fluids to inflate the balloon, it may be desirable to provide separate fluid delivery (i.e. inflation) and fluid withdrawal (i.e. deflation) conduits that open into the region between the balloon structure 125 and the inner flexible tubular element 111. Of course the separate fluid conduits can be formed in a wide variety of ways. By way of example, they can readily be formed by dividing lumen 116 (as best seen in FIG. 2(c) into two segments). Appropriate pumps are then connected to the proximal ends of different fluid conduits to control the balloon appropriately. With this arrangement, the saline used to inflate the balloon can be withdrawn through the withdrawal conduit either concurrently with or prior to delivery of the radioactive fluid through the delivery conduit. After the desired amount of radiation exposure, the radioactive fluid may be withdrawn and saline inserted to flush the catheter of radioactive fluid. It should be appreciated that the number of conduits provided, the conduits used for delivery or withdrawal of a particular fluid and/or the ordering of the fluid delivery and withdrawal steps can be widely varied to meet the needs of a particular system.

In some applications it may be desirable to treat several vessel segments in one procedure. The described separate fluid delivery and fluid withdrawal conduits and ports help facilitate this as well. In the discussion above, the separate fluid delivery and withdrawal conduits are described in the context of the expansion balloon embodiment. However, it should be appreciated that the same concept applies equally well to the occlusion style and other catheters which contemplate infusing and withdrawing fluids directly into/from the vessel. For example, some of the ports can be used as infusion port while others are used as withdrawal ports. In one specific arrangement, specific ports are arranged to take serum samples, while others are arranged to deliver therapeutic agents. Alternatively, different ports can be used for different purposes.

The foregoing descriptions have concentrated primarily on the working end of distal end of the described catheters. Suitable hub arrangements are provided at the proximal end of the catheters. As will be appreciated by those skilled in the art, the construction of the proximal hub assemblies can and will vary widely depending on the needs of a particular system. Generally, the hub must include appropriate electrical connectors for the thermal sensors and fluid connectors for the fluid delivery tubes. It also includes a valve (such as a Tuohy Borst valve) suitable for passing the guide wire and providing a fluid seal around the guide wire.

Figure 10:
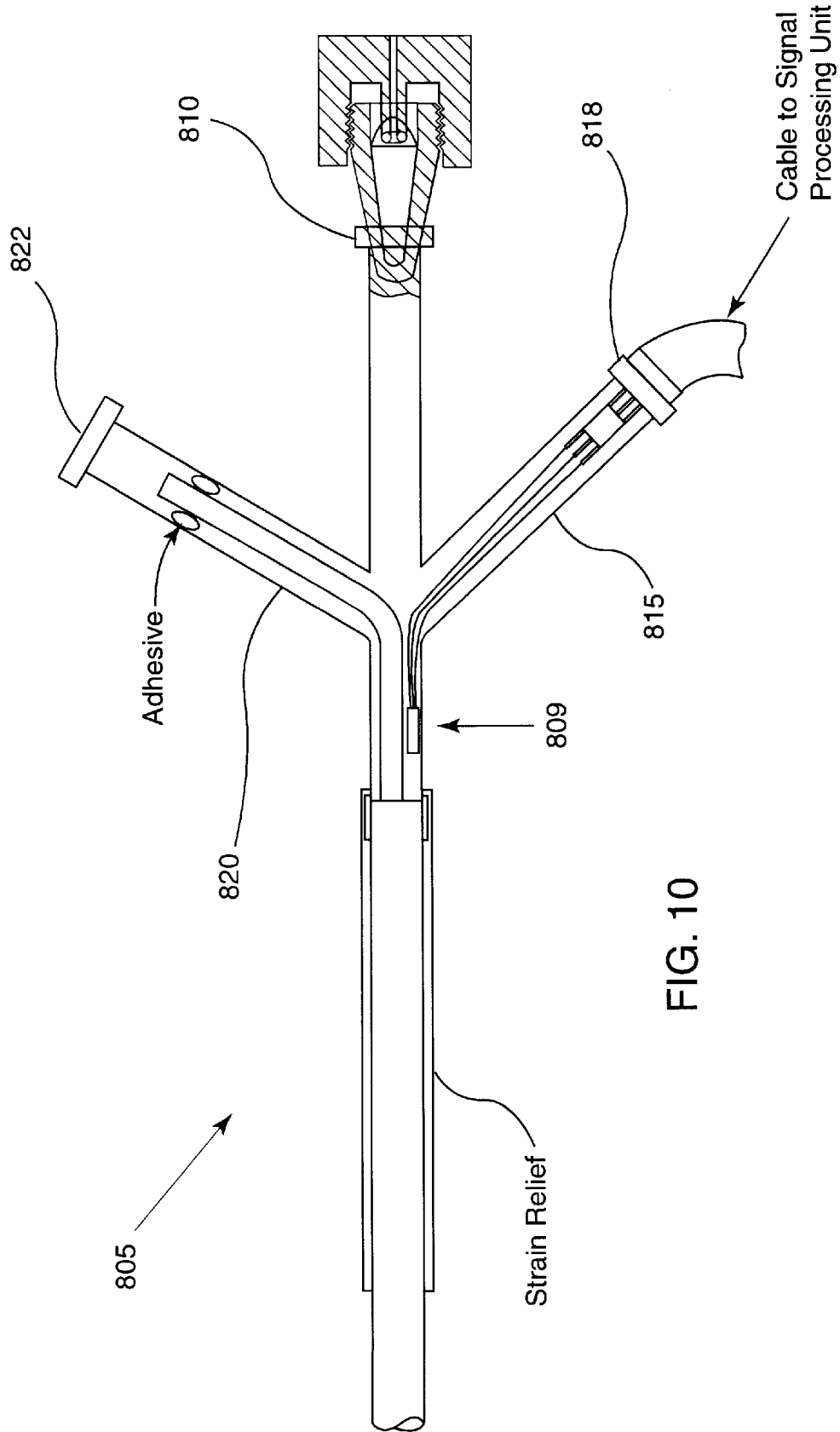
FIG. 10 is a side view of a proximal hub assembly suitable for use with some of the described catheters.

FIG. 10 illustrates one representative hub assembly that may be used in conjunction with some of the described catheters. In the embodiment shown, the proximal hub 805 includes a central arm 809 having a guide wire valve 810, an electrical sensor arm 815 having an electrical connector 818, and an inflation arm 820 having a luer connector 822. The central arm extends straight from the catheter to facilitate insertion of the guide wire therethrough. Conventional guide wire valves such as a Tuohy Borst valve can be used to create a fluid seal. The electrical connector 818 couples the thermal sensor wires to an appropriate interconnect cable attached to the data acquisition instrumentation (which preferably includes a display as illustrated in FIG. 11). By way of example, a conventional Lemo multi-pin connector works well as the electrical connector 818. The luer connector 822 provides a fluid seal between the inflation device and the balloon inflation lumen of the catheter.

Of course, in other embodiments which include infusion and/or withdrawal capabilities, additional arms would need to be provided to facilitate appropriate fluid communication pathways between the catheter and external controller and/or pumps. Similarly, if separate inflation and deflation conduits are provided, it may be desirable to provide additional hub arms to facilitate these connections as well.

Referring next to FIG. 11, a monitor suitable for displaying thermal maps will be described. The monitor 900 includes a display screen 904 suitable for displaying a thermal map 906. The monitor also includes a connector 908 that couples to the electrical connector 818 on the hub assembly and a number of control buttons 914.

Although only a few embodiments of the present invention have been described in detail, it should be understood that the present invention may be embodied in many other specific forms without departing from the spirit or scope of the invention. For example, in the embodiments shown, the sensors are generally arranged in uniformly spaced rows and/or bands. However, it should be apparent that the sensors could be arranged in a wide variety of patterns, including both nonuniformly spaced and non-aligned patterns without departing from the spirit of the invention. Further, although specific thermal mapping catheter constructions have been described, components of the various designs may in many cases be mixed and matched as appropriate to meet the needs of a particular application.

The examples above utilize thermisters or thermocouples as the thermal sensors. It should be appreciated that a variety of sensors may be used alternatively, including infrared sensors, luminescence absorption sensors and thermal cameras. However, thermisters and thermocouple-based systems are particularly advantageous because of their compactness and simplicity of function. Thermisters in particular have a reputation for very high sensitivity and are available in very small sizes. Thermocouples are somewhat less sensitive than thermisters, but are known for durability and very small size.

In the discussions above, frequent mention is made of the use of agents that may be delivered using the integrated drug delivery catheters. It should be appreciated that these devices can readily be used to deliver any type of agents, including therapeutic, diagnostic, marking agents, radioactive agents or any other type of agent that may be appropriate for a particular procedure.

The described thermal mapping catheters can be provided or combined with a number of other capabilities beyond the fluid delivery and/or withdrawal capabilities described in some detail above. By way of example, imaging capabilities, such as ultrasonic imaging, angioscopy or angiography may be desirable. In other applications, it may be desirable to combine the thermal mapping with the delivery of a stent or patch.

As pointed out above, the literature suggests that vulnerable plaque and other tissues of interest may have temperature signatures that are on the order of 0.5 to one degree centigrade higher than surrounding tissues or less. In some situations, the temperature variations may be somewhat higher, but it is expected that in most cases, the temperature differential will be less than two to four degrees centigrade. As further research is conducted and additional indicators are identified, it is suspected that even smaller temperature differential may have diagnostic significance. Therefore, the present examples are to be considered as illustrative and not restrictive, and the invention is not to be limited to the details given herein, but may be modified within the scope of the appended claims.

What is claimed is:

1. A catheter suitable for measuring the temperature of a vessel wall in the body of a patient, the catheter comprising:

an elongated flexible tubular member suitable for insertion in a vessel in the body of a patient, the flexible tubular member having proximal and distal ends;

a plurality of thermal sensors suitable for detecting the temperature of the wall of a vessel the elongated flexible tubular member is inserted into;

an expansion device carried by the flexible tubular member that carries the thermal sensors, the expansion device being suitable for positioning the thermal sensors adjacent the vessel wall; and a sheath/member that covers the thermal sensors such that at least some of the thermal sensors are positioned between the expansion device and the sheath/member when the thermal sensors are positioned for detecting the temperature of the vessel wall.

2. A catheter suitable for measuring the temperature of a vessel wall in the body of a patient, the catheter comprising:

an elongated flexible tubular member suitable for insertion in a vessel in the body of a patient, the flexible tubular member having proximal and distal ends;

a plurality of thermal sensors suitable for detecting the temperature of the wall of a vessel the elongated flexible tubular member is inserted into;

a first balloon carried by the flexible tubular member that carries the thermal sensors, the first balloon being suitable for positioning the thermal sensors adjacent the vessel wall; and a second balloon material that covers the thermal sensors such that the thermal sensors are positioned between the first balloon and the second balloon material; and wherein the thermal sensors are sandwiched between the first balloon and the second balloon material.

3. A thermal mapping and drug delivery system including:

an elongated a catheter comprising flexible tubular member suitable for insertion in a vessel in the body of a patient, the flexible tubular member having proximal and distal ends, a plurality of thermal sensors suitable for detecting the natural temperature of the wall of a vessel the elongated flexible tubular member is inserted into to facilitate thermal mapping of the vessel to identify naturally occurring temperature variation in the vessel wall, and at least one infusion port suitable for delivering therapeutic or diagnostic agents into a vessel, and a display device arranged to receive signals from the thermal sensors and display a thermal map of a longitudinal section of the vessel that shows temperature variations along the vessel.

4. A combined thermal mapping and drug delivery catheter comprising:

an elongated flexible tubular member suitable for insertion in a vessel in the body of a patient, the flexible tubular member having proximal and distal ends:

a plurality of thermal sensors suitable for detecting the temperature of the wall of a vessel the elongated flexible tubular member is inserted into;

at least one infusion port suitable for delivering therapeutic or diagnostic agents into a vessel; and wherein at least some of the infusion ports are located between adjacent thermal sensors.

5. A combined thermal mapping and therapeutic agent delivery system including comprising:

a catheter comprising an elongated flexible tubular member suitable for insertion in a vessel in the body of a patient, the flexible tubular member having proximal and distal ends, a multiplicity of thermal sensors suitable for detecting the natural temperature of the wall of a vessel that the elongated flexible tubular member is inserted into to facilitate thermal mapping of the vessel to identify naturally occurring temperature variation in the vessel wall, wherein a plurality of the thermal sensors are longitudinally spaced, an expansion device carried by the flexible tubular member, the expansion device being suitable for positioning the thermal sensors against the vessel wall, and at least one infusion port suitable for delivering therapeutic or diagnostic agents into a vessel, the infusion port being positioned between selected thermal sensors to facilitate delivering therapeutic or diagnostic agents into a vessel in the region of the thermal sensors, and a display device arranged to receive signals from the thermal sensors and display a thermal map of a longitudinal section of the vessel that shows temperature variations along the vessel.

6. A combined thermal mapping and therapeutic agent delivery catheter comprising:

an elongated flexible tubular member suitable for insertion in a vessel in the body of a patient, the flexible tubular member having proximal and distal ends;

a multiplicity of thermal sensors suitable for detecting the temperature of the wall of a vessel that the elongated flexible tubular member is inserted into, wherein a plurality of the thermal sensors are longitudinally spaced;

an expansion device carried by the flexible tubular member, the expansion device being suitable for positioning the thermal sensors against the vessel wall;

at least one infusion port suitable for delivering therapeutic or diagnostic agents into a vessel, the infusion port being positioned between selected thermal sensors to facilitate delivering therapeutic or diagnostic agents into a vessel in the region of the thermal sensors; and wherein at least some of the infusion ports are located longitudinally between selected ones of the thermal sensors.

7. A combined thermal mapping and therapeutic agent delivery catheter comprising:

an elongated flexible tubular member suitable for insertion in a vessel in the body of a patient, the flexible tubular member having proximal and distal ends;

a multiplicity of thermal sensors suitable for detecting the temperature of the wall of a vessel that the elongated flexible tubular member is inserted into, wherein a plurality of the thermal sensors are arranged in a plurality of longitudinally spaced bands, with each band having a plurality of circumferentially spaced thermal sensors;

an expansion device carried by the flexible tubular member, the expansion device being suitable for positioning at least some of the thermal sensors against the vessel wall; and a plurality of infusion ports suitable for delivering therapeutic or diagnostic agents into a vessel in the region of the thermal sensors, wherein at least some of the infusion ports are located between adjacent thermal sensor bands.

8. A combined thermal mapping and therapeutic agent delivery catheter comprising:

an elongated flexible tubular member suitable for insertion in a vessel in the body of a patient, the flexible tubular member having proximal and distal ends;

a multiplicity of thermal sensors suitable for detecting the temperature of the wall of a vessel that the elongated flexible tubular member is inserted into, wherein a plurality of the thermal sensors are longitudinally spaced;

an expansion device carried by the flexible tubular member, the expansion device being suitable for positioning the thermal sensors against the vessel wall, wherein the expansion device is arranged to include a plurality of recesses in an expanded position; and at least one infusion port suitable for delivering therapeutic or diagnostic agents into a vessel, wherein the infusion ports open into the recesses and are positioned between selected thermal sensors to facilitate delivering therapeutic or diagnostic agents into a vessel in the region of the thermal sensors.

9. A combined thermal mapping and therapeutic agent delivery catheter as recited in claim 8 wherein the expansion device includes a balloon arrangement and the recesses extend circumferentially around the balloon arrangement.

10. A combined thermal mapping and therapeutic agent delivery catheter comprising:

an elongated flexible tubular member suitable for insertion in a vessel in the body of a patient, the flexible tubular member having proximal and distal ends;

a multiplicity of thermal sensors suitable for detecting the temperature of the wall of a vessel that the elongated flexible tubular member is inserted into, wherein a plurality of the thermal sensors are longitudinally spaced;

an expansion device carried by the flexible tubular member, the expansion device being suitable for positioning the thermal sensors against the vessel wall; and at least one infusion port suitable for delivering therapeutic or diagnostic agents into a vessel, the infusion port being positioned between selected thermal sensors to facilitate delivering therapeutic or diagnostic agents into a vessel in the region of the thermal sensors;

a fluid delivery channel for delivering the therapeutic agents to the infusion port; and a reversible pump coupled to a proximal end of the fluid delivery channel to facilitate pumping the therapeutic agents into a vessel in the region of the thermal sensors, and thereafter withdrawing the therapeutic agents.

11. A thermal mapping catheter comprising:

an elongated flexible tubular member suitable for insertion in a vessel in the body of a patient, the flexible tubular member having proximal and distal ends;

a plurality of thermal sensors suitable for detecting the temperature of the wall of a vessel the elongated flexible tubular member is inserted into; and at least one anchoring balloon positioned either proximally or distally of the plurality of thermal sensors, the anchoring balloon being suitable for inflation during temperature sensing to occlude the flow of blood through the vessel.

12. A thermal mapping catheter as recited in claim 11 wherein a pair of anchoring balloons are provided, a first one of the anchoring balloons being positioned distally of the thermal sensors and a second one of the anchoring balloons being positioned proximally of the thermal sensors, the anchoring balloons being suitable for cooperating to isolate a segment of the vessel in the region of the thermal sensors.

13. A thermal mapping catheter as recited in claim 12 further comprising at least one infusion port suitable for delivering therapeutic or diagnostic agents into the vessel.

14. A method of obtaining a fluid specimen comprising:

inserting a catheter into a vessel;

using the catheter to detect the temperature of vessel walls to identify a target region within the vessel; and using the catheter to obtain a fluid specimen from the target region of the vessel.

15. A method of obtaining a fluid specimen as recited in claim 14 further comprising the step of isolating a vessel segment prior to obtaining the fluid specimen, wherein the fluid specimen is taken from the isolated vessel segment.

16. A method of treating vulnerable plaque comprising the steps of:

inserting a catheter into an artery;

using the catheter to detect the temperature of walls of the artery to identify a target region of vulnerable plaque; and applying a radioactive fluid to the target region of vulnerable plaque using the catheter to facilitate treatment of the vulnerable plaque.

17. A method as recited in claim 16 wherein the radioactive fluid is administered in a manner such that not more than about ten Gray of gamma or beta radiation is delivered to the target region of vulnerable plaque.

18. A method as recited in claim 16 wherein the radioactive fluid further includes one selected from the group consisting of: antibodies, anti-inflammatory agents and anti-thrombotic agents.

19. A catheter suitable for measuring the temperature of a vessel wall in the body of a patient, the catheter comprising:

an elongated flexible tubular member suitable for insertion in a vessel in the body of a patient, the flexible tubular member having proximal and distal ends;

a plurality of independent longitudinally spaced thermal sensors suitable for detecting the temperature of the wall of a vessel that the elongated flexible tubular member is inserted into, the thermal sensors being arranged to output signals suitable to provide a thermal map of a longitudinal section of the vessel.

20. A thermal mapping system including:

catheter as recited in claim 19; and a display device arranged to receive the signals from the thermal sensors and display a thermal map of a longitudinal section of the vessel that shows temperature variations along the vessel.

* * * * *